(12) United States Patent
Cannon et al.

(10) Patent No.: US 12,303,594 B2
(45) Date of Patent: *May 20, 2025

(54) ANTIMICROBIAL AND ANTI-INFLAMMATORY COMPOSITIONS

(71) Applicants: The Texas A&M University System, College Station, TX (US); The Board of Regents of the University of Texas System, Austin, TX (US)

(72) Inventors: Carolyn L. Cannon, College Station, TX (US); Parth N. Shah, College Station, TX (US); Justin A. Smolen, College Station, TX (US); Hugh D. Smyth, Westlake, TX (US); Ashkan K. Yazdi, Austin, TX (US); Matthew J. Herpin, Austin, TX (US)

(73) Assignees: The Texas A&M University System, College Station, TX (US); The Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/219,090

(22) Filed: Jul. 7, 2023

(65) Prior Publication Data
US 2023/0346697 A1 Nov. 2, 2023

Related U.S. Application Data

(63) Continuation of application No. 15/576,485, filed as application No. PCT/US2016/034906 on May 29, 2016, now Pat. No. 11,723,864.

(60) Provisional application No. 62/168,561, filed on May 29, 2015.

(51) Int. Cl.
| A61K 9/00 | (2006.01) |
| A61K 31/19 | (2006.01) |
| A61K 45/06 | (2006.01) |
| A61K 47/12 | (2006.01) |
| A61P 29/00 | (2006.01) |

(52) U.S. Cl.
CPC .......... *A61K 9/0078* (2013.01); *A61K 9/0075* (2013.01); *A61K 31/19* (2013.01); *A61K 45/06* (2013.01); *A61K 47/12* (2013.01); *A61P 29/00* (2018.01)

(58) Field of Classification Search
CPC ...... A61K 9/0078; A61K 47/16; A61K 31/19; A61K 45/06; A61K 9/0075; A61P 29/00
See application file for complete search history.

(56) References Cited

U.S. PATENT DOCUMENTS

| 6,051,566 A | 4/2000 | Bianco |
| 2004/0018252 A1 | 1/2004 | Shahinian |
| 2012/0160944 A1 | 6/2012 | Dodd et al. |
| 2014/0050739 A1 | 2/2014 | Francois et al. |
| 2014/0065219 A1 | 3/2014 | Bosch et al. |
| 2014/0234310 A1 | 8/2014 | Shapiro |
| 2014/0326812 A1 | 11/2014 | Dodd et al. |

FOREIGN PATENT DOCUMENTS

| WO | WO-0182906 A1 * | 11/2001 |
| WO | WO 2008/139170 | 11/2008 |
| WO | WO-2008/139170 A2 | 11/2008 |

* cited by examiner

*Primary Examiner* — Shirley V Gembeh
(74) *Attorney, Agent, or Firm* — Winstead PC

(57) ABSTRACT

The claimed invention is directed to the use of a composition for use as an antimicrobial comprising an antimicrobial agent. In certain embodiments, the composition is used for treating or ameliorating inflammation in a subject and comprises an anti-inflammatory agent. The anti-inflammatory agent may include an NSAID, such as ibuprofen or diclofenac. The composition may further include solvents, anti-bacterial agents, anti-fungal agents, anti-parasitic agents, anti-viral agents, and buffers. The composition may include particles that have been processed via jet milling to reduce a diameter of the particles and to improve a flowability of the particles.

7 Claims, 5 Drawing Sheets

ANTIMICROBIAL AND ANTI-INFLAMMATORY COMPOSITIONS

CROSS-REFERENCES TO RELATED APPLICATIONS

This application is a continuation of U.S. application Ser. No. 15/576,485 filed on Nov. 22, 2017, which claims the benefit under 35 U.S.C. § 119(e) of U.S. Provisional Patent Application No. 62/168,561, filed May 29, 2015, each of which is incorporated herein by reference in its entirety as if fully set forth herein.

TECHNICAL FIELD

The present invention relates generally to the treatment of inflammatory disease and/or infectious disease and, more specifically, to compositions comprising compounds having antimicrobial and/or anti-inflammatory activity and therapeutic uses thereof.

BACKGROUND OF THE INVENTION

Inflammation is a component of the pathogenesis of a number of human diseases, as well as a result of physical, chemical or traumatic damage (i.e., inflammation is the response of living tissue to damage). In general, the inflammatory response results in the systemic release of endogenous chemical mediators, which cause vasodilatation, emigration of neutrophils, chemotaxis, and increased vascular permeability. The changes that result from an inflammatory response are essentially the same, regardless of the cause and regardless of where the insult arises. The inflammatory response may be acute (short lived) or chronic (longer lasting).

The development of inflammatory reactions is controlled by cytokines, by products of the plasma enzyme systems (complement, coagulation, kinin, and fibrinolytic pathways), by lipid mediators (prostaglandins and leukotrienes) released from different cells, and by vasoactive mediators released from mast cells, basophils and platelets. Fast-acting mediators, such as vasoactive amines and the products of the kinin system, modulate the immediate response. Later, newly synthesized mediators such as leukotrienes are involved in the accumulation and activation of other cells. Once leukocytes have arrived at a site of inflammation, they release mediators that control the later accumulation and activation of other cells. Thus, the cytokine system is clearly important for homeostasis when cytokine activation is local (i.e., acting nearby as a surface-bound or diffusible form), but when cytokine production is sustained and/or systemic, there is no doubt that cytokines contribute to the signs, symptoms, and pathology of inflammatory, infectious, autoimmune, and malignant diseases.

Typically, an inflammatory response is beneficial because the site of inflammation will have increased access to nutrients, oxygen, antibodies and therapeutic drugs, as well as increased fibrin formation, dilution of toxins, and stimulation of an immune response. However, an inflammatory response may have negative consequences, such as tissue damage caused by the release of lysosomal enzymes by inflammatory cells (neutrophils and macrophages) or an inappropriate response may result in a life threatening hypersensitivity reaction (e.g., asthma or anaphylaxis).

Accordingly, such detrimental inflammatory responses (often referred to as inflammatory diseases) are often treated with anti-inflammatory drugs. There are two major types of anti-inflammatory drugs, corticosteroids and non-steroidal anti-inflammatory drugs (NSAIDs). However, a detrimental consequence of therapies with corticosteroids and NSAIDs is an inhibition of neutrophil trafficking and a reduction in pathogen killing, which can be particularly dangerous in, for example, an immunocompromised patient. In another example, many people suffer the symptoms of Cushing's syndrome as a side effect of taking corticosteroids for asthma, rheumatoid arthritis, lupus, or other inflammatory diseases. Similarly, NSAIDs have side effects, such as causing anaphylactoid reactions and causing gastrointestinal and renal toxicity. Nephrotoxicity with systemic, high-dose ibuprofen can be a problem in patients with cystic fibrosis (CF), who are frequently on other nephrotoxic drugs, such as aminoglycosides.

Ibuprofen (IBU) is one such NSAID indicated for pain, fever, and other inflammatory conditions such as osteoarthritis, rheumatoid arthritis, and pericarditis. Even though IBU holds promise in the management of CF, the use of this treatment modality has not been well-adopted or widespread. Diclofenac (DF) is another NSAID that is indicated for analgesia, osteoarthritis, rheumatoid arthritis, migraine, and other inflammatory disorders. It has been commonly formulated as its sodium and potassium salts, i.e. diclofenac sodium (DFNa) and diclofenac potassium. The DF salts are marketed as tablets, capsules, or solutions for oral administration, solutions for intravenous administration, solutions for ophthalmic administration, and as creams, gels, patches and solutions for topical administration.

Despite the availability of NSAIDs as over-the-counter (OTC) medications, there are multiple contraindications, black-box warnings, and general warnings regarding their use. Gastrointestinal (GI) adverse drug reactions (ADRs) such as an increased risk of upper gastrointestinal bleeding associated with the use of NSAIDs is well documented. Two primary contraindications for the use of NSAIDs are the treatment of perioperative pain following coronary artery bypass graft surgery and the use in patients with moderate to severe renal impairment. Recently, the United States' Food and Drug Administration (FDA) strengthened their warning about the risk of NSAIDs causing heart attacks or stroke. The risk of heart attacks and strokes is increased as early as the first few weeks of NSAID use, and risk level is drug-, dose- and duration-dependent. Finally, there is an increased risk of heart failure with NSAID use.

Delivery via the lung represents a unique opportunity to circumvent the prostaglandin (PG) independent mucosal injury associated with the oral administration of NSAIDs, as it eliminates the direct GI exposures to these drugs. Furthermore, the pulmonary drug delivery route usually decreases the dose requirements by ten to twenty fold, especially for drugs acting locally on the lungs. Similar to the topical delivery, reducing the systemic exposure via pulmonary drug delivery, allows for the minimization of the cardiovascular risks as well as the systemic PG-dependent, GI adverse effects associated with NSAIDs. Finally, the rapid onset times that are seen with pulmonary drug delivery for both local and systemic effects are ideal for the patients, to whom NSAIDs are prescribed.

Typically with inhaled powders, such as inhaled corticosteroids and β-adrenergic agonists, it has been found that the binary blends of micronized drug with a lactose carrier system significantly improve their performance. This type of formulation approach may not be feasible for inhaled NSAIDs. Despite the ten to twenty fold total dose reduction facilitated by local lung delivery of DF, the required doses will still be in the milligram range, greater than the upper limit for common binary dry powder inhaler (DPI) formulations. An example of a carrier-free inhaled product is the Tobi® Podhaler™, containing low-density spray dried particles, which are highly engineered. Particle engineering is the primary technique for improving the aerosol performance of carrier-free DPI formulations, through the reduction of aerodynamic diameter. Equation 1 describes the relationship between the aerodynamic diameter (Dae), the diameter of equivalent volume sphere (Deq), the particle density (rp), the unit density (ro), and the dynamic shape factor (x).

$$D_{ae} = D_{eq}\sqrt{\frac{\rho_p}{\rho_p x}}$$ Equation (1)

Therefore, a need exists for identifying agents having anti-inflammatory activity that are not immunosuppressive and/or cause other undesirable side effects. Furthermore, there is a need for agents having both antimicrobial activity and anti-inflammatory activity for use in treating, preventing, or ameliorating infectious diseases where concomitant inflammation is a problem, such as in cystic fibrosis. Such agents would be useful in a variety of clinical indications having an inflammatory component.

SUMMARY OF THE INVENTION

The present invention provides compounds and combinations of compounds and methods for using such compounds in a variety of therapeutic settings, such as in treating, preventing, or ameliorating, for example, local or systemic inflammatory diseases associated with acute inflammation or chronic inflammation.

In one aspect, the present invention provides a compound that has anti-inflammatory and/or anti-microbial properties. In another aspect, the present invention provides a combination of compounds, wherein one or more of the compounds in the combination has anti-inflammatory and/or anti-microbial properties.

In another aspect there is provided a composition comprising any one of the aforementioned compounds, or a combination thereof, and a pharmaceutically acceptable excipient. In another embodiment, the aforementioned composition further comprises a buffering agent. In still another embodiment, the composition further comprising a buffering agent has a pH ranging from about 3 to about 8. In yet another embodiment, the viscosity-increasing agent is dextran, polyvinylpyrrolidone, hydroxyethyl cellulose, or hydroxypropyl methylcellulose.

In other embodiments, any of the aforementioned compositions may comprise a solvent, wherein the solvent is selected from the group consisting of water, glycerin, isopropanol, and ethanol. In further embodiments, any of the aforementioned compositions may further comprise a preservative. In a further embodiment, any of the aforementioned compositions may comprise a preservative comprising benzoic acid, benzyl alcohol, phenoxyethanol, methylparaben, propylparaben, or a combination thereof. As used herein, any reference to an acid may include a free acid, a salt, and any ester thereof. In other embodiments, any of the aforementioned compositions further comprise a humectant and a preservative.

In a further aspect there is provided a method treating, preventing, or ameliorating inflammation at a target site, the method comprising applying to the target site any of the aforementioned compositions. In other embodiments, any of the aforementioned methods wherein the inflammation is acute, adhesive, atrophic, catarrhal, chronic, croupous, degenerative, exudative, fibrinopurulent, fibrinous, granulomatous, interstitial, necrotic, proliferative, pseudomembranous, purulent, sclerosing, serofibrinous, serous, or subacute. In further embodiments, any of the aforementioned methods wherein the inflammation at the target site is associated with a condition, wherein the condition is acne, arthritis, autoimmune disease, burn, Crohn's disease, colitis, contact hypersensitivity, cystic fibrosis, delayed type hypersensitivity, eczema, endotoxin shock syndrome, fibromyositis, graft rejection, lichen, microbial infection, multiple sclerosis, parapsoriasis, psoriasis, sclerosis, or seborrhea. In another embodiment, any of the aforementioned methods may comprise wherein the inflammation is associated with a medical device.

Pulmonary delivery may be an attractive alternative to high-dose oral administration in CF since lungs are the desired targets for the anti-inflammatory and antibiotic activities of IBU and inhalation therapy of other compounds is already well accepted in CF patients. The inhalation route is known to be associated with pharmacokinetic advantages, requiring a decreased administered dose for an equivalent pharmacological effect in the lungs compared to oral or systemic routes. In comparison with oral and systemic administrations, inhalation administration can provide a dosing advantage between 10 and 24 fold and may be able to minimize the systemic risks related to conventional high-dose IBU therapy. Furthermore, pulmonary delivery of IBU minimizes GI adverse drug reactions by eliminating direct GI toxicity. Typically with inhaled powders, a binary formulation of a drug with a carrier, such as lactose, significantly improves their performance. However, this strategy is not practical for the delivery of a large drug dose via a dry powder inhaler (DPI). Moreover, nebulizers can require significantly more time for drug delivery, and metered dose inhalers may be incapable of metering sufficiently large drug doses. Therefore, carrier-free DPIs have been explored.

The instant application describes delivering IBU in a carrier-free system. Jet-milled IBU samples were characterized, and effects of capsule-fill weight (i.e. loaded dose), air-jet milling batch size, and formulation aging/conditioning on the in vitro aerodynamic performance of carrier-free, high-dose DPI formulations of IBU were investigated. For simplicity, in these studies a capsule-based DPI was used. Capsule-based inhalation systems require individual capsules to have adequate powder loading in order to avoid multiple administrations and to decrease administration burden for high-dose DPI delivery. Previously, it has been shown that capsule-based DPI device air flow resistance is dependent on the capsule-fill weight. However, the effect of capsule-fill weight on in vitro aerodynamic performance has not been reported despite the knowledge that in vitro aerodynamic performance is affected by changes in device resistance. Furthermore, air-jet milling is considered a batch manufacturing process where batch size and batch-to-batch variability may significantly influence physicochemical characteristics of milled powders. Additionally, powder handling may affect these characteristics within a single batch. Even though these changes may not be detectable with standard characterization methods, they may affect performance of DPIs during formulations. Finally, milling disturbs integrity of crystalline material and post-milling storage alters particle size through "surface re-crystallization" and "stress relaxation." Surface re-crystallization of amorphous domains on adjacent particles, and resultant interparticulate bridges, increase effective particle size. Conversely, stress relaxation of milled material decreases particle size through introduction of new fractures and subsequent reorientation of molecules in crystalline structure. Both phenomena alter DPI performance, and their degree of presence should be evaluated during post-milling storage. It is believed that the in vitro aerodynamic performance, and thereby the expected in vivo performance, of carrier-free, high-dose DPI formulations may be affected by capsule-fill weight, air-jet milling batch size, and formulation aging.

These and other aspects of the present invention will become evident upon reference to the following description and attached drawings. In addition, various references are set forth herein which describe in more detail certain procedures or compositions, and are therefore incorporated by reference in their entirety.

DESCRIPTIONS OF THE DRAWINGS

For a more complete understanding of the present invention and for further objects and advantages thereof, reference may now be had to the following description taken in conjunction with the accompanying drawings in which.

DESCRIPTION OF THE INVENTION

Figure 1:
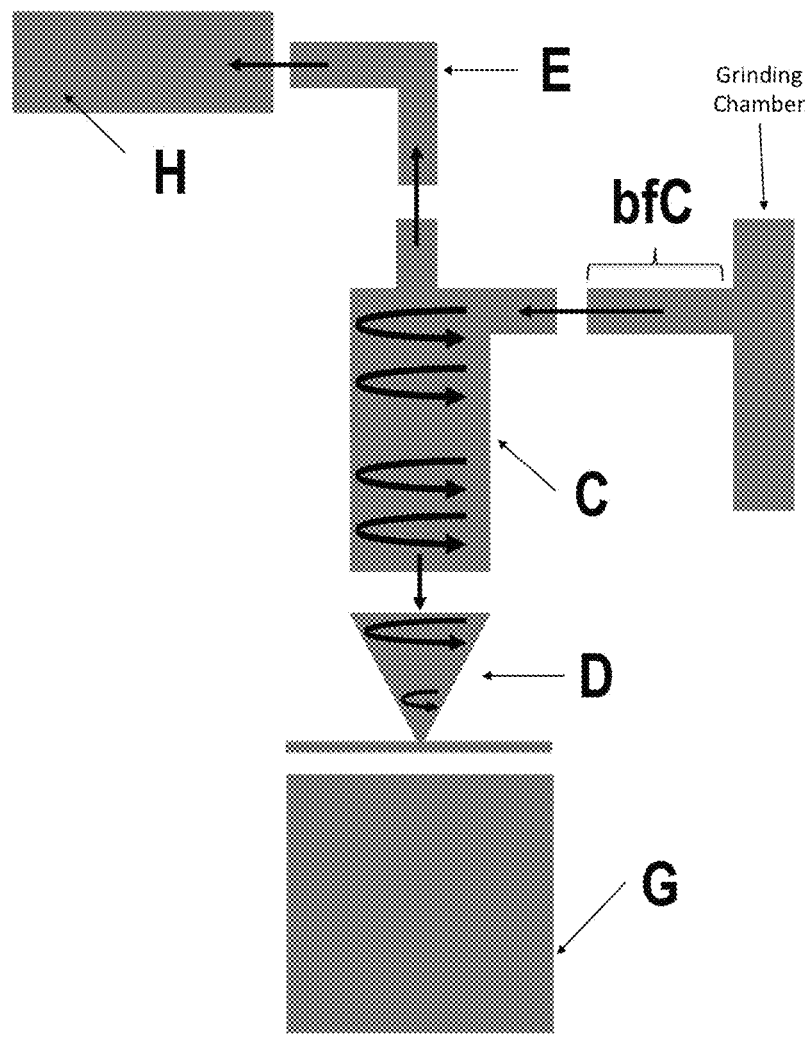
FIG. 1 is a schematic diagram of a configuration for a jet mill.

Various embodiments of the present invention will now be described more fully with reference to the accompanying drawings. The invention may, however, be embodied in many different forms and should not be construed as limited to the embodiments set forth herein.

As noted above, the present invention provides compounds, and compositions thereof, that exhibit antimicrobial and/or anti-inflammatory activity. These compounds can be formulated for use in methods for treating, preventing, and/or ameliorating acute or chronic inflammatory diseases. In certain embodiments, the compositions comprise NSAIDs either alone or in combination with anti-microbial compounds. The invention, therefore, relates generally to the surprising discovery that NSAIDs may be formulated at a clinically relevant concentration for use as an antimicrobial agent, as an anti-inflammatory agent, and as both an antimicrobial and anti-inflammatory agent, either alone or in combination with anti-microbial compounds. Thus, compositions of the present invention are useful for use in a variety of therapeutic settings, including without limitation, treatment, prevention, or amelioration of inflammatory and infectious diseases. Discussed in more detail below are compositions suitable for use within the present invention, as well as exemplary therapeutic uses.

Any concentration range recited herein is to be understood to include concentrations of any integer within the range and fractions thereof, such as one tenth and one hundredth of an integer, unless otherwise indicated.

The present invention is directed generally to compositions comprising compounds having antimicrobial and/or anti-inflammatory activity for use in treating, preventing, or ameliorating inflammatory diseases, as described herein. Suitable antimicrobial and/or anti-inflammatory compounds include, but are not limited to, NSAIDs.

The compositions of the present invention may be used with one or more conventional antimicrobial agents, as described herein. Thus, synergistic combinations of an antimicrobial and/or anti-inflammatory compound and an antimicrobial agent may permit a reduction in the dosage of one or both agents in order to achieve a similar or improved therapeutic effect. This would allow the use of smaller doses and, therefore, would decrease the potential incidence of toxicity and lowering costs of expensive antimicrobials. Concurrent or sequential administration of an antimicrobial and/or anti-inflammatory formulation and an antimicrobial agent and/or anti-inflammatory agent composition is expected to provide more effective treatment of infections, caused by a variety of microorganisms (e.g., bacteria, viruses, fungi, and parasites), and/or inflammatory diseases. In particular, successful treatment or prevention of infectious disease can be achieved by using the antimicrobial and/or anti-inflammatory compositions with antimicrobial agents and/or anti-inflammatory agents at doses below what is normally a therapeutically effective dose when these antimicrobials and anti-inflammatory agents are used individually. Alternatively, an antibiotic agent and/or anti-inflammatory agent with an antimicrobial and/or anti-inflammatory agent can be administered using a normally effective therapeutic dose for each active component, but wherein the combination of the two or more agents provides even more potent effects.

As noted above, the preferred antimicrobial and/or anti-inflammatory compositions may be used in a synergistic combination with other known antimicrobial agents. Antibacterial agents include, but are not limited to, penicillins, cephalosporins, carbacephems, cephamycins, carbapenems, monobactams, aminoglycosides, glycopeptides, quinolones, tetracyclines, macrolides, and fluoroquinolones.

The antimicrobial and/or anti-inflammatory compositions may also be used in combination with anti-fungal agents. Exemplary anti-fungal agents include, but are not limited to, terbinafine hydrochloride, nystatin, amphotericin B, griseofulvin, ketoconazole, miconazole nitrate, flucytosine, fluconazole, itraconazole, clotrimazole, benzoic acid, and selenium sulfide.

The antimicrobial and/or anti-inflammatory compositions may also be used in combination with anti-viral agents. Exemplary anti-viral agents include, but are not limited to, amantadine hydrochloride, rimantadin, acyclovir, famciclovir, foscarnet, ganciclovir sodium, idoxuridine, ribavirin, sorivudine, trifluoridine, valacyclovir, vidarabin, didanosine, stavudine, zalcitabine, zidovudine, interferon alpha, and edoxudine.

The antimicrobial and/or anti-inflammatory compositions may also be used in combination with anti-parasitic agents. Exemplary anti-parasitic agents include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole (sulfamethoxazole/trimethoprim), and pentamidine isethionate.

As noted above, the preferred antimicrobial and/or anti-inflammatory compositions may be used in a synergistic combination with other known anti-inflammatory agents.

Anti-inflammatory agents include, without limitation, oral or inhaled corticosteroids (e.g., hydrocortisone, triamcinolone), NSAIDs (e.g., nabumetone, indomethacin, naproxen, ibuprofen), anti-inflammatory cytokines (e.g., IL-4, IL-10, IL-13), cytokine antagonists (e.g., IL-1 receptor antagonist, TNF-α monoclonal antibody, soluble TNF receptor, platelet factor 4), and the like.

Uses of the antimicrobial and/or anti-inflammatory compositions of the present invention encompass numerous applications where an antimicrobial or anti-inflammatory agent is useful in the treatment, prevention, or amelioration of infection and/or inflammation. Preferably, a formulation comprising one or more anti-inflammatory agents and/or anti-microbial agents, are administered by inhalation. Systemic administration could also be via intravenous, intramuscular or subcutaneous injections or infusions. Other routes of administration known in the art could also be used.

Another use for the present compositions and methods is in the treatment of inflammation conditions that are often accompanied by microbial infections. Cystic fibrosis (CF) results from mutations in both alleles of the cystic fibrosis transmembrane conductance regulator (CFTR) gene. Chronic pulmonary infections occur with a variety of pathogens including Pseudomonas aeruginosa and Staphylococcus aureus, the major perpetrators of lung infection and the major causes of morbidity and mortality in patients with CF. The proportion of patients harboring antibiotic resistant strains of these organisms is climbing. These bacteria form biofilms in the CF lung, which in the case of P. aeruginosa, appear to result from selection of phenotypic variants with enhanced capacity for biofilm formation. These same variants are highly antibiotic-resistant compared with parent strains and may explain, in part, the observed number of CF patients who harbor multi-drug resistant Pseudomonas aeruginosa (MDR-PA). In 2009, 51.2% of CF patients exhibit P. aeruginosa infections, of which 9.8% of the patients are infected with MDR-PA. Furthermore, the proportion of CF patients colonized with methicillin-resistant Staphylococcus aureus (MRSA) continues to escalate, with 25.7% of the CF patients infected with S. aureus currently harboring an MRSA strain. Thus, chronic infection with increasingly resistant organisms poses one of the major challenges in the care of patients with CF.

Bacterial multi-drug resistance is an increasing problem, particularly for certain populations, such as CF patients. One of the major sources of multi-drug resistance is the multidrug efflux pump. These pumps confer resistance to a wide variety of antimicrobials by actively extruding them out of the bacterial cytoplasm and thereby reducing their intracellular concentration. These pumps are found across the spectrum of gram-positive and gram-negative bacteria, and they can act synergistically with other resistance mechanisms to greatly enhance the overall resistance phenotype. Since multidrug efflux pumps can interact with a large variety of antimicrobials, selection by one antimicrobial of a mutant with increased expression for such a pump often results in cross-resistance to other antimicrobials. In P. aeruginosa, for instance, upregulation of the MexXY-OprM efflux system can confer resistance to fluoroquinolones, carbenicillin, ceftazidime, and aminoglycosides. Thus, these efflux pumps are commonly responsible for multidrug resistant strains.

The problem of multi-drug efflux pumps has spurred interest in developing efflux-pump inhibitors (EPIs). Studies have identified a variety of novel compounds that act as EPIs, but none have been developed for clinical use, probably due to the high risk of developing new drugs. However, repurposing existing drugs that show an EPI effect and have well-established safety profiles is an effective strategy for abrogating much of this risk. Ibuprofen has been identified as a candidate for a type of EPI, based on its likely action as an uncoupler of oxidative phosphorylation. Uncouplers inhibit ATP production by shuttling protons across energy-transducing membranes, which rely on impenetrability to maintain a proton-gradient-based electromotive force for ATP-synthase to generate ATP from ADP during respiration. Among the various types of compounds that can have uncoupling activity, the most potent are weakly acidic, hydrophobic (typically aromatic) compounds that have the ability to delocalize negative charge in their anionic state. Most commonly used NSAIDs have these characteristics, and studies have demonstrated that weak-acid NSAIDs, including ibuprofen, cause uncoupling in mitochondria.

While uncouplers of oxidative phosphorylation are not direct EPIs—they do not directly inhibit efflux-pump proteins—they do indirectly interfere with efflux function by inhibiting energy production. Efflux mechanisms are dependent upon either energy from ATP or on the proton-motive force, and uncouplers inhibit both. By depleting the available energy in bacterial cells, uncouplers greatly reduce the activity of efflux pumps, resulting in higher drug accumulation. In fact, classic uncouplers are used as standard bench-top reagents for inhibiting antibacterial efflux-pump activity. Additionally, energy depletion from uncoupling has shown activity against other types of resistance that require ATP, such as the production of β-lactamases. Despite these benefits, classic uncouplers have not been sought out as potential EPI drugs, perhaps due to concern over toxicity. Many NSAIDs, however, have well-established safety and toxicity profiles and thus would be more attractive compounds for exploiting this effect.

The synergy between ibuprofen and certain antimicrobials in both P. aeruginosa and S. aureus has been demonstrated that supports the hypothesis of an EPI effect from uncoupling. In addition to the synergistic effects of ibuprofen. an antimicrobial effect with in vitro bacterial growth studies has also been demonstrated.

The synergistic and direct antimicrobial properties of ibuprofen, and likely other NSAIDs, make it very appealing as an adjuvant treatment for CF infections. Studies have already thoroughly demonstrated that ibuprofen has benefits for CF patients, such as slowing lung-function decline. While these studies concluded that the benefits of ibuprofen result from its anti-inflammatory effects, these new findings of antimicrobial activity could add to the explanation of ibuprofen's benefits. However, despite ibuprofen's proven safety and demonstrated efficacy, high-dose ibuprofen is used by only a minority of CF patients in the United States, primarily due to the inconvenience of required pharmacokinetic studies and the concern regarding the risk of gastrointestinal bleeding and nephrotoxicity.

Drug inhalation has a number of benefits for treating lung infections in that it is a relatively easy, non-painful procedure that provides localized delivery of drugs to the site of action, the airways of the lungs. Localized delivery allows for lower total doses of drug to be used while maintaining high concentrations where needed. Thus, inhalation delivery helps increase efficacy while decreasing systemic toxicity including the risk of nephrotoxicity.

An embodiment of the present invention is directed to a micronized formulation of an NSAID obtained via jet-milling. Jet milling transforms the NSAID from a powder with a Flow Property rating lower than almost very, very poor flow to one with a Flow Property rating of almost good flow (Table 1). Such an improvement is contrary to common teaching that micronization reduces particle flow. Improved powder flow is important for the ability to accurately dose powder during manufacturing of unit doses, for example in capsules for use in dry powder inhalers or to enable accurate dosing using a reservoir dry powder inhaler that contains a metering mechanism. Advantages of micronization of the NSAID include: ability to be inhaled in the respiratory tract and airways, usage in undiluted, pure form, enabling higher doses and less frequent administration; NSAIDS like ibuprofen have been proven to be effective in cystic fibrosis patients in high oral doses. These high doses are often associated with higher side effects especially gastrointestinal bleeding. Inhaled ibuprofen overcomes these limitations and allows patients to achieve similar benefits; and inhaled ibuprofen may be synergistic with other inhaled therapeutics such as antibiotics.

In addition to cystic fibrosis, inflammatory lung conditions such as asthma, emphysema, and chronic obstructive pulmonary disease (COPD) for which local anti-inflammatory actions are desirable could be disease targets for such a formulation. Furthermore, pulmonary administration in systemic disease states would also be desirable where NSAIDs' gastrointestinal tract related adverse events are to be avoided and/or more immediate responses are desired.

In certain embodiments of the invention, the NSAID of the claimed composition is used an antimicrobial alone. In certain embodiments, the NSAID is micronized such that the powder flow is suitable for filling into pharmaceutical dosage units. The flow of the micronized NSAID is improved compared to that of the bulk powder.

In certain embodiments of the invention, the micronized NSAID powder is administered by inhalation. In certain embodiments, the micronized powder does not contain any additional excipient. In some embodiments, the micronized powder has a unit dose of greater than 10 mg. In other embodiments the micronized powder has a unit dose of at least 10 mg.

In certain embodiments of the claimed invention, the micronized NSAID compositions have aerosol efficiencies of greater than 50%, greater than 60% or greater than 70%, as measured by the fraction of fine particles. In certain embodiments, the particle size of the NSAID particles is designed to not dissolve rapidly in biological fluids, which in turn increases the residence time at the place of administration.

In certain embodiments of the claimed invention, the NSAID composition comprise additional antimicrobial compounds that act synergistically in their antimicrobial activities with the NSAID.

In certain embodiments, the NSAID composition is formulated with at least one pharmaceutically acceptable acid to reduce the pH of the NSAID suspension for inhalation. The acid may be citric acid or hydrochloric acid with the resulting composition having a pH of less than 5, less than 3 and less than 2.

In certain embodiments, the buffering capacity of the pH-adjusted composition is either low or not buffered.

In certain embodiments, the NSAID compound is used as a solvent carrier for an anti-infective compound. In this embodiment, the NSAID is melted in the presence of the anti-infective compound such that the anti-infective compound dissolves in the NSAID which is then cooled to form particles.

WORKING EXAMPLES

Formulations that could make use of NSAID/antimicrobial synergy for treatment of lung infection include:

- Polymeric nano- or micro-particles, liposomes, and micelles that co-encapsulate both the NSAID and antimicrobial and are delivered via inhalation in dry powder or suspended in solution and nebulized.
- Polymeric nano- or micro-particles, liposomes, and micelles that encapsulate the NSAID and antimicrobial separately, but are mixed together and delivered as one dry powder formulation or one suspended solution to be nebulized.
- Polymeric nano- or micro-particles, liposomes, and micelles that encapsulate the NSAID only but are delivered with free antimicrobial in dry powder or suspended in solution and nebulized.
- Dry powder mixtures of NSAID and antimicrobial.

Embodiments of the invention are directed to the preparation of NSAID formulations that are capable of being administered directly to airways through direct inhalation via a metered dose inhaler, dry powder inhaler or nebulizer. An embodiment of the invention is a micronized ibuprofen formulation via jet-milling (median size=2.72 µm, span=1.80 compared with Ibuprofen, USP available through the supplier, median size=48 µm, span=1.84) with significantly improved bulk flow identified by Angle of Repose (37.8°±5° compared with 62.6°±2.9° for the Ibuprofen, USP available through the supplier) and surprising superior aerodynamic performance (For 25 mg capsules, Emitted Dose Fraction (EDF)=72.3±1.8%, Fine Particle Fraction (FPF)=73.2±3.2%, Respirable Fraction (RF)=52.2±0.8%). Its major use will be for the carrier-free DPI formulation of IBU for chronic use in cystic fibrosis (CF) with anti-inflammatory and anti-microbial effects.

Jet-milling significantly improved bulk flow identified by Angle of Repose (37.8°±5° compared with 62.6°±2.9° for the Ibuprofen, USP available through the supplier) transforms ibuprofen from a powder with almost very, very poor flow to one with almost good flow (Table 1). Such improvement is contrary to common teaching that micronization reduces particle flow.

Such improvement in flow is accompanied with surprisingly superior aerodynamic performance for a carrier free formulation in which no major changes in particle density have been introduced. For 25 mg capsules, EDF=72.3±1.8%, FPF=73.2±3.2%, RF=52.2±0.8%. Furthermore, powder bulk density and tap density measurements for the jet-milled vs commercial ibuprofen are as followed: 0.117 vs. 0.268 and 0.212 vs. 0.441 g/cm$^3$.

TABLE 1

Flow Properties and Corresponding Angles of Repose

| Flow Property | Angle of Repose (°) |
| --- | --- |
| Excellent | 25-30 |
| Good | 31-35 |
| Fair-Aid not needed | 36-40 |
| Passable-May hang up | 41-45 |
| Poor-Must agitate, vibrate | 46-55 |
| Very poor | 56-65 |
| Very, very poor | >66 |

Compressibility Index (CI) and Hausner Ratio (HR) were calculated accordingly and are as follows: 45.000 vs 39.189 and 1.818 vs. 1.644. However, the calculated CI greater than 25 and HR greater than 1.25 are indicative of poor flowability according to the common belief which does not agree with the surprising performance and angle of repose calculations.

TABLE 2

| Scale of Flowability | | |
|---|---|---|
| Compressibility Index (%) | Flow Property | Hausner Ratio |
| ≤10 | Excellent | 1.00-1.11 |
| 11-15 | Good | 1.12-1.18 |
| 16-20 | Fair | 1.19-1.25 |
| 21-25 | Passable | 1.26-1.34 |
| 26-31 | Poor | 1.35-1.45 |
| 32-37 | Very poor | 1.46-1.59 |
| >38 | Very, very poor | >1.6 |

Synergy has been demonstrated between ibuprofen and certain antimicrobials in both *P. aeruginosa* and *S. aureus* that further supports the hypothesis of an EPI effect from uncoupling. Endpoint time-kill synergy studies against two resistant strains (PA HP3 and SA 25-05) were performed by growing inoculums of $5*10^5$ CFU/ml in Mueller Hinton (MH) broth with or without ibuprofen and with or without a sub-MIC concentration of an antimicrobial. The strains were grown in a shaking incubator (37° C., 200 rpm) for 6 hours (SA 25-05) or 9 hours (PA HP3). Afterwards, the inoculums were plated to determine their CFU/ml. Synergy from the combination was determined by a $≥2×log_{10}$ decrease in CFU/ml when compared to antimicrobial treatment alone. Ibuprofen significantly increased the killing efficacy of both ceftazidime and gentamicin against these resistant bacteria.

In addition to the synergistic effects of ibuprofen, a mild antimicrobial effect with in vitro bacterial growth studies and with in vivo survival and bacterial-burden studies has been demonstrated. Various gram-negative bacterial strains (*Pseudomonas aeruginosa*, PA01: *Burkholderia multivorans*, BM; and an *Escherichia coli* strain. EC J53+pmg101) were cultured in Mueller Hinton (MH) broth to a density of $5*10^5$ colony forming units (CFU)/ml as verified by serial dilution and growth of colonies on tryptic soy agar (TSA) plates. The bacterial culture was aliquoted into 96-well plates (100 μL/well) and a low-dose treatment solution of 10 μg/mL or 1 μg/mL ibuprofen in a 5% DMSO. 95% distilled water solution or a control of just the DMSO/water solution was added in a 1:1 (v:v) ratio. Cultures were grown at 37° C. and, at discrete time points, the optical density at 600 nm (OD600) was measured via spectrophotometer as a measure of bacterial growth. At these concentrations, ibuprofen slowed and/or delayed the growth of all the tested strains. Endpoint CFU counting was also performed on PA01 and a *Staphylococcus aureus* vancomycin-intermediate (VISA) strain (Mu50). For these studies, inoculums at $5*10^5$ CFU/ml were grown in MH in a shaking incubator for 6 hours (37° C. 200 rpm) and then plated to count CFU. Significant reduction in CFU was found for both PA01 and Mu50 when treated with ibuprofen.

The antibiotic effects of ibuprofen were further demonstrated in vivo using a mouse model of acute, *P. aeruginosa* pneumonia. In these studies, male C57/BL6 mice, aged 6-8 weeks, were sedated (ketamine/xylazine) and inoculated intranasally with PA01 using a dose calibrated to result in an $LD_{50}$ ($3-8×10^5$ CFU). After 2 hours and every 8 hours thereafter, the mice were fed via syringe with either ibuprofen suspended in flavored syrup (0.75 mg in 100 μL) or syrup only. To determine the effect of ibuprofen on in vivo bacterial counts, the mice were euthanized (sedation with Avertin® and cervical dislocation) at 36 hours post-infection and their lungs and spleens were harvested and homogenized, using serial dilutions plated onto tryptic soy agar (TSA) to determine CFU counts. Significant reductions in both lung and spleen bacterial burdens were observed for the mice treated with ibuprofen. Also, the mice were weighed and assigned clinical scores, a semi-quantitative metric that rates their signs of infection from asymptomatic (0) to moribund (6), at the start of the study, at 12 hours, and at the termination of the study. While no significant effect on weight loss after infection was observed, ibuprofen did significantly reduce the clinical scores, probably in part due to analgesic effects. Ibuprofen also improves survival rates after *P. aeruginosa* infection, as demonstrated in an in vivo survival study. For this study, the mice were administered treatment on the same schedule and were observed continuously for their time of death over the course of 72 hours, by the end of which any surviving mice begin to recover. Again, ibuprofen demonstrated antibiotic efficacy with a significant survival advantage for the treated mice (92%) vs. control (57%). Also, the ibuprofen-treated mice had less weight loss on day 3 and significantly better clinical scores on days 2 and 3.

The synergistic and direct antimicrobial properties of ibuprofen, and likely other NSAIDs, make it very appealing as an adjuvant treatment for CF infections. Indeed, studies have already thoroughly demonstrated that ibuprofen has benefits for CF patients, such as slowing lung-function decline. While these studies concluded that the benefits of ibuprofen result from its anti-inflammatory effects, these new findings of antimicrobial activity could add to the explanation of ibuprofen's benefits. However, despite ibuprofen's proven safety and demonstrated efficacy, high-dose ibuprofen is used by only a minority of CF patients in the United States, primarily due to the inconvenience of required pharmacokinetic studies and the concern regarding the risk of gastrointestinal bleeding.

We have addressed the concerns of NSAID-induced gastrointestinal bleeding by looking to inhalation (via nebulization) as a route of delivery. Drug inhalation has a number of benefits for treating lung infections in that it is a relatively easy, non-painful procedure that provides localized delivery of drugs to the site of action, the airways of the lungs. Localized delivery allows for lower total doses of drug to be used while maintaining high concentrations where needed. Thus, inhalation delivery helps increase efficacy while decreasing systemic toxicity.

While some drugs are water soluble and readily nebulizable as a free drug, such as tobramycin (TOBI™), many drugs are hydrophobic and thus not easily nebulized. Most NSAIDs are highly hydrophobic, and in terms of taking advantage of their effects as uncouplers, this hydrophobicity is integral. One method for nebulizing hydrophobic drugs is to formulate an aqueous solution that can solubilize it. Such a solution was formulated using a small amount of DMSO (1% v/v) and phosphate ($PO_4$) buffer. This solution is capable of solubilizing ibuprofen up to a concentration of 5 mg/ml. Using this solution, the pharmacokinetics of nebulized delivery of free ibuprofen was explored. To perform this study, healthy, male C57BL-6 mice—aged 6-8 weeks—were distributed randomly by weight into 3 groups with 3 mice per group: 25 mg ibuprofen, 50 mg ibuprofen, and sham. The mice were placed within CH-247 tubes, which ensure nose-only delivery of the nebulized mist, and then placed into the nebulizer box. The ibuprofen was dissolved in the aforementioned solution and the mice were nebulized with it using an Aerogen Aeroneb™ micro-pump nebulizer, which produces an aerosol mist with a droplet diameter between 1-5 μm. The nebulization occurred over a period of 45-70 minutes. Immediately after nebulization, the mice were delivered an intraperitoneal injection of Avertin™ to bring them to complete sedation, as verified by toe-pinch. The mice were then dissected and euthanized via cardiac puncture, with the blood collected into serum-separator tubes and centrifuged at 1.000 g for 10 minutes to collect the serum. Bronchial alveolar lavage fluid (BALF) was collected with 3 ml of sterile $PO_4$ buffer injected into and aspirated from the lungs via the trachea using a catheter and syringe. Then, the whole lung tissue was harvested and homogenized in 1 ml of sterile $PO_4$ buffer. The collected serum, BALF, and lung tissue were then measured for urea content (BioVision®), which allows for the concentrations of ibuprofen (or other drugs) to be normalized to a true volumetric concentration, since urea concentrations should be constant throughout the body. Finally, the ibuprofen concentrations were determined using an ELISA kit (Neogen®) against a standard of ibuprofen dissolved in the 99% $PO_4$ buffer/1% DMSO solution used for nebulization.

The concentrations of ibuprofen in the serum. BALF, and lung tissue were studied. The ibuprofen was rapidly taken up by the blood, with serum concentrations 12-15× higher than BALF concentrations and 4-5× higher than lung-tissue concentrations. This rapid uptake into the blood is consistent with previous observations of lung delivery of hydrophobic small-molecule compounds. Based on the serum ibuprofen concentrations and a predicted blood volume of 1.5 ml for a 25 g mouse, approximately 0.8% of the 25 mg dose and 1.0% of the 50 mg dose were delivered to the mice. The slightly higher delivered percentage of the 50 mg dose may be explained by the fact that the higher ibuprofen dose took longer to nebulize, and thus the mice would have had longer exposure to the mist. Overall, these results demonstrate that nebulization of free ibuprofen is not a feasible method for treating lung infection, since the vast majority of the ibuprofen is rapidly lost from the lungs into the serum. Instead, a formulation of ibuprofen that can retain its residence in the airways of the lungs upon inhalation is desirable.

Since nebulized delivery of free ibuprofen results in poor residence time within the lungs, the development of ibuprofen-encapsulating nanoparticles for inhalation delivery has been explored. Numerous advantages of nanoparticle drug delivery have been recognized. In a general sense, incorporation of a drug within nanoparticles through physical encapsulation. chemical conjugation or adsorption improves the pharmacokinetics and therapeutic index of the drug compared with its free drug counterpart. Such drug delivery systems also offer the possibility of concurrently delivering multiple therapeutic agents at a sustained or controlled rate to target organs and/or tissues of interest. Furthermore, the controlled release aspect of nanoparticulate drug delivery formulations lower the frequency of drug administration, thus affording improved patient concordance. Nanoparticulate formulations also provide a highly effective means to improve mass transfer from the particle into the surrounding medium, and thus improve the bioavailability of insoluble/poorly soluble hydrophobic drugs. Along with the potential of reducing toxicity, direct administration of antimicrobials to the lungs as nanoparticle formulations can aid in reducing the problem of antimicrobial resistance, since a high localized concentration of the drug can be maintained while overcoming the rapid clearance of the drug from the lungs.

We have formulated ibuprofen-loaded nanoparticles using a mixture of two biodegradable polymer systems: poly (lactide-coglycolide) (PLGA) and a copolymer of PLGA and poly (ethylene glycol) (PEG) (PLGA-PEG). PLGA was used to formulate the core of the nanoparticles because it is biodegradable, FDA-approved for human therapy, has extended release rates from days to months, has mechanical properties that are amenable to forming nanoparticles, and is extensively used for intravenous administration of therapeutic agents. However, nanoparticles comprised of only PLGA have a tendency to be rapidly shuttled to the liver and spleen by macrophages in the mononuclear phagocyte system, limiting their circulation time and thus the effectiveness of the encapsulated drug. This effect can be reduced by incorporation of PEG on the nanoparticle surface. PEG is an FDA-approved polymer that has no known debilitating effects, is widely known as a biological 'stealth' agent, and is extensively used in the formulation of drug delivery devices, especially for the purpose of surface modification of nanoparticles. This 'stealth' quality refers to its ability to protect a particle's surface from non-specific opsonization by certain plasma components, inhibiting recognition by phagocytes of the reticuloendothelial system (RES). The reduction in immune recognition by PEGylation leads to longer circulation times, from 32 minutes with PLGA to over 15 hours with PLGA-PEG, thus increasing drug effectiveness. Furthermore, PEG has been shown to increase nanoparticle diffusion through human mucoid surfaces, increasing their ability to penetrate into the deep mucus layers, even bacterial biofilm, and thus bypassing one of the protective barriers bacteria utilize against antimicrobials in the CF lung. The addition of PEG to the surface of the nanoparticles can be accomplished through simple blending of PLGA-PEG with PLGA. During the emulsion-based nanoparticle formulation process, the hydrophobic PLGA segment of PLGA-PEG is energetically favored to associate with the PLGA in the hydrophobic core: whereas, hydrophilic PEG segments are favored to project from the particle surface into the surrounding aqueous medium, creating a sterically stabilizing layer.

Ibuprofen-loaded PLGA: PLGA-PEG NPs have been formulated using the oil-in-water emulsion technique. For this procedure, the polymers (PEG-PLGA and PLGA) were dissolved in 3 ml chloroform (100 mg/ml) along with the ibuprofen (10 mg/ml). The organic solution was emulsified with 100 ml polyvinylprrolidone (PVP) solution (10% w/v in water) loaded with or without the sodium salt of ibuprofen, to improve loading, for 3 minutes with high-speed mechanical stirring, after which the emulsion was gently stirred at room temperature for 5 hours to remove the organic solvent. As the solvent diffused into the aqueous solution and evaporates, the nano-sized polymer-and-drug droplets hardened, trapping the drug within the polymer matrix. The resulting nanoparticle suspension was centrifuged and washed—removing excess surfactant and drug molecules bound to the particle surface—shell-frozen, and lyophilized to process the nanoparticles into a free-flowing powder. The NPs were layered onto carbon tape coated stubs, sputter coated with gold, and visualized using an FEI XL30 ESEM at an accelerating voltage of 15 kV. The resulting nanoparticles have a nice spherical morphology and demonstrated a particle size distribution ranging from a few hundred nanometers to approximately 3 pn in diameter for the nanoparticles generated without sodium ibuprofen. Nanoparticles generated with sodium ibuprofen in the external phase had a narrower particle size distribution with most particles being sub-micron sized in diameter. Loading studies of the nanoparticles were performed by dissolving the particles in CHC13, diluting 50× in $DH_2O$, and measuring ibuprofen content with the forensic ELISA kit. The nanoparticles loaded without sodium ibuprofen contained ~4% ibuprofen by weight, while those loaded with sodium ibuprofen contained 16% ibuprofen by weight.

In order to determine whether the antimicrobial activity is preserved for ibuprofen upon formulation into nanoparticles, an endpoint CFU study was performed. Ibuprofen nanoparticles, blank nanoparticles, and a control solution was added to planktonic suspensions of PA01 at $5*10^5$ CFU/ml in MH at a concentration of nanoparticles determined by their ibuprofen loading (500 µg/ml theoretical ibuprofen concentration) or an equivalent mass of blank nanoparticles. The suspensions were placed in a shaking incubator for 6 hours (37° C., 200 rpm) and then plated to count CFU. Significant reductions in CFU from control were found for treatment with the ibuprofen/sodium ibuprofen-loaded nanoparticles and to a lesser extent for the ibuprofen-loaded nanoparticles. No significant difference in CFU from control was found for suspensions treated with blank nanoparticles.

Overall, nanoparticle co-formulation of ibuprofen with currently available antimicrobials shows much promise as a treatment against resistant bacteria in the lungs. Ibuprofen shows strong synergistic activity with two common antimicrobials, ceftazadime and gentamicin, against two of the most problematic bacteria for patients with CF, *P. aeruginosa* and *S. aureus*. If this effect is proven to be a result of ibuprofen acting as an uncoupler of oxidative phosphorylation, then other NSAIDs are highly likely to produce similar results, since NSAIDs in general are known to have uncoupler activity. Once other NSAID/antimicrobial combinations are tested for synergy against a variety of CF-relevant, resistant bacteria strains, the best combinations will be determined and co-formulated into nanoparticles. Then, the nanoparticle formulations can be applied to mouse models to gauge their efficacy against lung infection as well as their safety/toxicity profile. Soon after, we envision that the safest/most efficacious formulations would be rapidly translatable and commercializable.

Solid pure ibuprofen nanoparticles have been formulated that are suitable for pulmonary delivery. The idea behind this approach is to formulate ibuprofen nanoparticles with FDA-approved excipients (inactives) so as to allow rapid translation to the clinic and avoid costly and protracted safety studies of new inactives. We have developed and begun to characterize such aerosolizable solid drug nanoparticles of ibuprofen capable of providing depot delivery to the lung.

Two novel formulation methods, which control the processing conditions to produce stabilized drug particles with acceptable excipients without requiring organic solvents, have been developed. The first method is a novel Melt Sono-Emulsification process where molten ibuprofen is dispersed into an aqueous phase containing a pulmonary surfactant. An emulsion is formed under rotor-stator homogenizer for 10 minutes followed by probe ultrasonication. The nanoemulsion is cooled to solidify the molten droplets. The emulsion is then diluted with cooled aqueous surfactant solution to capture the particles, which results in small NPs with verified short-term stability. The second method is Communition by Novel High Pressure Homogenization, where ibuprofen particles are first dispersed in water. Since water is an incomplete anti-solvent for ibuprofen, we use a novel pH and temperature controlled method to ensure nanoparticle stability. The particles are gradually reduced in size by passing through a high-pressure homogenizer multiple times, resulting in particles larger than those obtained by the previous method, but with better stability.

Ibuprofen release studies were performed using nanoparticle suspensions formulated by the Communition method. The release profile appears to be promising for pulmonary delivery of ibuprofen, a small molecular weight drug with high lipophilicity, which is rapidly absorbed from the lung into the circulation. Thus, the advantage of prolonged lung exposure achieved through sustained delivery will potentially enhance the therapeutic effects. We have also characterized the aerosolization efficiency of the formulated nanoparticle suspension using an Aeroneb Pro nebulizer. A relatively high dose (10 mg) of ibuprofen was nebulized in slightly less than 5 minutes and analysis of the nebulate using UVNis spectroscopy at 266 nm demonstrated an output efficiency of 93.25%. Lastly, aerosol particle size determination performed using laser diffraction of the nebulate showed a median particle diameter of 4.48 microns, which is suitable for inhalation.

Spray-drying processing can be utilized to produce microparticles of ibuprofen using a novel set of parameters; however, due to the softness and the low melting point of ibuprofen and thereby processing condition limitations, particle size may not be reduced less than 15 µm where ibuprofen solution of ethanol is spray-dried.

The microparticles discussed herein may be produced by the methods outlined below:

Jet-Milling of Ibuprofen (Microparticles)

5, 10, or 20 g of unprocessed ibuprofen was micronized using a labscale Aljet mill at a feed rate 1 g/min for the unprocessed ibuprofen with compressed nitrogen to provide the kinetic energy for micronization with a feed pressure of 65 psi and grinding pressures of 75 psi at both grinding nozzle feeds. Collection bag fraction with 16% yield and with d50 of 2.72 µm and span=1.80 (compared with d50 of 48 µm and span=1.84 for the unprocessed ibuprofen) and surface area of 2.28±0.077 $m^2/g$ (compared with 0.357±0.005 $m^2/g$ for unprocessed ibuprofen) was used to conduct Next Generation Impactor aerodynamic performance testing, angle of repose testing, bulk and tap density measurements. Angle of repose for micronized ibuprofen was 37.8°±5 (compared with 62.6°±2.9° for the unprocessed ibuprofen). Bulk and tab density of micronized ibuprofen were 0.117 and 0.212 $g/cm^3$ (compared with 0.268 and 0.441 g/cm3 for unprocessed ibuprofen) and CI and HR were calculated as 45 and 1.82 (compared with 39.2 and 1.64 for unprocessed ibuprofen). Surprising aerodynamic performance with fine particle fraction ($FPF_5$ µm) of 73.2±3.2% was observed for carrier free dry powder inhaler (DPI) formulation with 25 mg capsule load using high resistance RSO1 capsule based DPI.

Jet-Milling of Indomethacin (Microparticles)

5 g of unprocessed indomethacin was micronized using a labscale Aljet mill at a feed rate 1 g/min for the unprocessed indomethacin with compressed nitrogen to provide the kinetic energy for micronization with a feed pressure of 65 psi and grinding pressures of 75 psi at both grinding nozzle feeds. Cyclone fraction with 43% yield and with d50 of 4.04 µm and span=1.90 (compared with d50 of 26.3 µm and span=2.25 for the unprocessed indomethacin and surface area of 2.4±0.11 $m^2/g$ (compared with 0.435±0.039 $m^2/g$ for unprocessed indomethacin) was used to conduct Next Generation Impactor aerodynamic performance testing, angle of repose testing, bulk and tap density measurements. Angle of repose for micronized indomethacin was 41.5°±8.8° (compared with 57.4°±4.3° for the unprocessed indomethacin). Bulk and tab density of micronized indomethacin were 0.194 and 0.361 $g/cm^3$ (compared with 0.321 and 0.580 $g/cm^3$ for unprocessed indomethacin) and CI and HR were calculated as 46.3 and 1.86 (compared with 44.7 and 1.81 for unprocessed indomethacin) Surprising aerodynamic performance with fine particle fraction ($FPF_5$ µm) of 82.1±1.1% was observed for carrier free dry powder inhaler (DPI) formulation of micronized indomethacin with d50 of 1.24

μm and span=1.69 (collection bag fraction) with 10 mg capsule load using high resistance RSO1 capsule based DPI.

Jet-Milling of Diclofenac (or Other NSAIDs) (Microparticles)

5 g of unprocessed diclofenac is micronized using a labscale Aljet mill at a feed rate 1 g/min for the unprocessed diclofenac with compressed nitrogen to provide the kinetic energy for micronization with a feed pressure of 65 psi and grinding pressures of 75 psi at both grinding nozzle feeds yielding particles with d50 less than 5 sm and angle of repose less than 35-45°.

Co Spray-Drying of Ibuprofen and Ciprofloxacin (Microparticles)

2 g of Ciprofloxacin HCl is dissolved in 100 mL water and is added to 2 g of Ibuprofen dissolved in 100 mL of Ethanol. Ethanol is removed using rotary evaporator and the resultant mixture is spray-dryed to yield microparticles composed of ciprofloxacin HCl and Ibuprofen. Resultant microparticles are characterized and aerodynamic performance is evaluated using NGI.

Set forth below are several exemplary methods and formulations of the claimed invention.

Example 1

Method and Composition:

- High Pressure Homogenization by Avestin Emulsiflex C5
- Pre-Homogenization for 10 minutes at 10,000 rpms at ~4 C using a rotor stator homogenizer.
- Instrument Conditions: 5 passes at 250 bar, followed by 5 passes at 500 bar, 10 passes @1500 bar, (sampled) and ran for a final 10 passes @ 1500 bar Formulation:

- 400 mg of Ibuprofen raw powder
- 60 mg Tween 80
- 40 mL of 0.44% Citric Acid

Example 2

Melt Sono-Emulsificiation

Instrument Conditions:

Equipment: Misonix Sonicator Misonix 600 W

- Duty Cycle: 50-50
- Power: 40 W
- 5 minutes
- Sample Temp: 80° C.
- Cooled to 4° C. in ice bath under stirring Formulation:

- 500 mg Ibuprofen raw powder
- 0.05% Tween 80
- 0.1N HCL

Example 3

Molten Ibuprofen as a Solvent for Ciprofloxacin:

Process: Melt pure ibuprofen in a small beaker, then slowly add ciprofloxacin till completely dissolved. Then slowly add 0.5% Tween in 0.1N HCl solution under stirring (preheated to 80° C.). Finally, Sonicate in similar conditions as in example 2.

Formulation:

- 250 mg Ibuprofen raw powder
- 250 mg Ciprofloxacin
- 0.05% Tween 80
- 0.1N HCL

Example 4

Spray Drying of Nanosuspension produced in Example 1 to produce microparticles comprising nanoparticles bound together by citric acid and tween 80.

Example 5

A method for disc diffusion assay includes the following: The activity of five antibiotics (amikacin, aztreonam, ceftazidime, colistin, and tobramycin) was assessed against three strains of *Pseudomonas aeruginosa* (PAM57-15, PAO1 and PA HP3) using a disc diffusion assay. A single colony of *P. aeruginosa* was picked and grown to an optical density at 650 nm ($OD_{650}$) of 0.4. A 100 μL aliquot of inoculum was spread over Mueller-Hinton (MH) agar plates, as well as MH agar plates supplemented with 100 μg/mL ibuprofen. Discs containing known quantities of the five previously mentioned antibiotics were placed on the two types of agar plates and incubated for 18 hours. The diameters of the zones of inhibition were measured and compared between the MH and MH+IBU plates.

Example 6

A method for minimum inhibitory concentrations (MIC) includes the following: The bacteria were diluted in the standard MH broth to a concentration of $5\times10^5$ in 100 μL, which was added to triplicate wells of 96-well plates containing various concentrations of aztreonam, ceftazidime or vancomycin solutions prepared from 10 mg/mL stocks in MH broth. The final concentrations of aztreonam, ceftazidime and vancomycin were 0.06, 0.13, 0.25, 0.5, 1, 2, 4, 8, 16, 32, 64, and 128 μg/ml. The plates were incubated overnight at 37° C. The MIC was the lowest of these concentrations at which each of the triplicate wells in each 96-well plate was clear after 16-24 hours of incubation. Each triplicate was performed at least twice.

Example 7

A method for checkerboard assay includes the following: The bacteria were diluted in the standard MH broth to a concentration of $5\times10^5$ in 100 μL, which was added to each well of a 96-well plate. Aztreonam, ceftazidime and vancomycin solutions were prepared from 10 mg/mL stocks in MH broth. Ibuprofen was prepared from 10 mg/mL stocks in MH with the presence of dimethyl sulfoxide (DMSO). The final concentrations of aztreonam were 0.5, 1, 2, 4, 8, and 16 μg/mL; the final concentrations of ceftazidime were 2, 4, 8, 16, 32, and 64 μg/mL and the final concentrations of vancomycin were 0.25, 0.5, 1, 2, 4, 8, and 16 μg/mL. The final concentrations of ibuprofen were 50, 75, and 100 μg/mL. All wells contained a final concentration of DMSO of 0.125%. Each descending row of a 96-well plate contained an increased concentration of a single antibiotic, either aztreonam, ceftazidime or vancomycin, starting at zero from the top of the plate. Each set of triplicate columns starting at the left-most columns of the same plates contained increasing concentration of ibuprofen starting at zero. The plates were incubated and read as noted for the MIC assay. Again, each triplicate was performed at least twice.

Example 8

A 24 hour end point colony forming units (CFU) count study was performed. The bacteria were diluted in the standard MH broth to a concentration of 5×10[5] CFU in 100 µL, which was added to triplicate wells of a 96-well plate, containing various concentrations of aztreonam or ceftazidime plus ibuprofen. The dilutions of aztreonam, cefazidime, and ibuprofen were made from 10 mg/mL stock in MH broth; the ibuprofen stocks contained 0.5% DMSO. The final concentrations of aztreonam were 1, 2, 4, and 8 µg/mL; the final concentrations of ceftazidime were 2, 4, 8, and 16 µg/mL; and the final concentrations of ibuprofen were 50, and 100 µg/mL. Again, all wells contained a final concentration of DMSO of 0.125%. Increasing concentrations of aztreonam and ceftazidime were loaded horizontally into each well of two separate 96-well plates starting with zero at the top of the plate. Ibuprofen was loaded vertically from left to right in triplicate wells of the antibiotic-loaded 96-well plates starting at zero. The plates were set on a platform shaker at 100 rpm in a 37° C. warm room for 24 hours. After the 24-hour incubation, each well was diluted by taking 50 µl culture into 450 µl of MH broth. A 50 µl aliquot of each dilution was plated on blood agar. This serial dilution step was repeated seven times for each well to reach countable numbers of colonies on the blood agar plates.

The diameters of the zones of inhibition significantly increased on the MH agar plate with 100 µg/mL ibuprofen compared with the MH agar control plates in the presence of aztreonam (P=0.0346) and ceftazidime (P=0.0462) against the *P. aeruginosa* strain PA HP3.

The MIC of aztreonam against PA HP3 is 4 µg/mL. The MIC of ceftazidime against PA HP3 is 16 µg/mL. The MIC of vancomycin against MRSA 0646 is 2 µg/mL. The synergistic MIC of aztreonam is 2 µg/mL with the presence of 50 µg/mL of ibuprofen. The synergistic MIC of ceftazidime is 4 µg/mL with the presence of 50 µg/mL of ibuprofen. The synergistic MIC of vancomycin is 1 µg/mL with the presence of 50 µg/mL of ibuprofen (e.g., see Table 3).

TABLE 3

MICs of aztreonam and ceftazidime against *Pseudomonas aeruginosa* (strain PA HP3) with or without presence of ibuprofen. MIC of vancomycin against methicillin-resistant *Staphylococcus aureus* (strain MRSA 0646) with and without the presence of ibuprofen.

|  | MIC (µg/mL) | MIC (with ibuprofen) (µg/mL) |
|---|---|---|
| Aztreonam against PA HP3 | 4 | 2 (50) |
| Ceftazidime against PA HP3 | 16 | 4 (50) |
| Vancomycin against MRSA 0646 | 2 | 1 (50) |

The fractional inhibitory concentration (FIC) index is generally defined as follows: (MIC of drug A, tested in combination)/(MIC of drug A, tested alone)+(MIC of drug B, tested in combination)/(MIC of drug B, tested alone). Interaction are defined as synergistic if the FIC index is <1, additive if the FIC index is =1 and antagonistic if the FIC index is >1. Because it has been found that the MIC of ibuprofen against these strains is >128 µg/mL, the FIC for aztreonam+ibuprofen is ½+(<50/128), which is <1, the combination is synergistic. Similarly, the FICs for cefatzidime and vancomycin are both less than 1 signifying that these combinations are also synergistic.

The CFU end-point studies demonstrate that in the presence of either 50 or 100 µg/mL ibuprofen in 1 µg/mL of aztreonam, the CFU counts of PA HP3 decreased significantly (P<0.0001) compared to the CFU counts of 1 µg/mL aztreonam alone. In the presence of 50 or 100 µg/mL ibuprofen in 2 or 4 µg/mL of ceftazidime, the CFU counts decreased significantly (P<0.0001) compared to the CFU counts of 2 or 4 µg/mL ceftazidime alone.

Example 9

The influence of capsule-fill weight, batch size, and storage conditions on in vitro aerodynamic performance of jet-milled ibuprofen (IBU) carrier-free dry powder inhaler formulations were investigated.

Milled and unmilled IBU samples were characterized thermally and spectroscopically. Physicochemical characterization was performed by quantifying specific surface area, density, and angle of repose. Performance testing was conducted on IBU formulations in combination with a high resistance Monodose RSO1 using Next Generation Impactor.

Unprocessed IBU, United States pharmacopoeia (USP) (Letco Medical, Decatur, Alabama) served as a control in the physicochemical characterization. IBU samples were micronized via air-jet milling (Model 00 Jet-O-Mizer™ also known as Aljet mill, Fluid Energy, Telford, PA, USA). The samples included the milled IBU from 5, 10, and 20 g batches (IBU5, IBU10.1, IBU10.2, IBU20) as depicted in Table 4.

TABLE 4

The $D_{10}$, $D_{50}$, $D_{90}$, and span values for 5, 10, and 20 g batches of jet-milled ibuprofen (IBU5, IBU10.1, IBU10.2, IBU20).

| Notation | Batch (g) | $D_{10}$ (μm) | $D_{50}$ (μm) | $D_{90}$ (μm) | Span |
|---|---|---|---|---|---|
| IBU5 | 5 | 0.8 | 1.9 | 3.6 | 1.5 |
| IBU10.1 | 10 | 0.9 | 2.2 | 4.2 | 1.5 |
| IBU10.2 | 10 | 1.0 | 2.7 | 7.6 | 2.4 |
| IBU20 | 20 | 1.1 | 2.7 | 6.0 | 1.8 |

The particle size distribution (PSD) $D_{10}$, $D_{50}$, and $D_{90}$ values for each sample were defined as particle diameters at the 10th, 50th, and 90th percentile and the span value was calculated according to Equation 2:

$$\text{Span} = \frac{D_{90} - D_{10}}{D_{50}} \qquad \text{Equation (2)}$$

Scanning electron microscopy (SEM): The milled samples (IBU5, IBU10.1, IBU10.2, and IBU20) were mounted on standard aluminum SEM stubs, were sputter coated with 15 nm platinum/palladium (Pt/Pd) using a Cressington sputter coater 208 HR (Cressington Scientific Instruments Ltd., Watford, UK) and were imaged using a Zeiss Supra 40VP SEM (Carl Zeiss Microscopy GmbH, Jena, Germany).

X-Ray powder diffraction (XRD): Two-dimensional X-Ray diffractograms for the milled samples (IBU5, IBU10.1, IBU10.2, and IBU20) were obtained using an automatic R-Axis Spider (Rigaku Corporation, Tokyo, Japan), an X-ray single crystal diffractometer controlled by RINT Rapid software with target radiation of Copper at 40 KV voltage and 40 mA current. The samples were suspended in light mineral oil and were loaded on loops epoxied to conventional goniometer bases. Additionally, a background X-Ray diffractogram of light mineral oil loaded on the loops was subtracted from sample diffractograms, one-dimensional 2θ diffractograms were generated, and .txt files were saved using 2DP Software (Ragaku Corporation, Tokyo, Japan). To analyze the one-dimensional diffractograms using Jade (Ragaku Corporation, Tokyo, Japan), .raw files were generated from .txt files using the ConvX.exe (Mark Bowden, Industrial Research Ltd., Lower Hutt, New Zealand).

Differential scanning calorimetry (DSC): For the sample IBU20 and unmilled IBU, thermograms were obtained using an Auto Q20 (TA Instruments-Waters LLC, New Castle, DE, USA) differential scanning calorimeter controlled by the TA Advantage Software (TA Instruments-Waters LLC, New Castle, DE, USA) and equipped with a RCS40 (TA Instruments-Waters LLC, New Castle, DE, USA) refrigerated cooling system with nitrogen purge of 50 mL/min. About 4 mg of each sample were loaded in standard DSC pans (DSC Consumables Inc., Austin, MN, USA) and were crimped using a Tzero sample press (TA Instruments-Waters LLC, New Castle, DE, USA). Samples were heated at the rate of 10° C./min from 30° C. to 100° C.

Fourier transform infrared spectroscopy (FT-IR): For the sample IBU20 and unmilled IBU, FT-IR spectra were obtained using a Nicolet™ iSTM50 FT-IR Spectrometer (Thermo Fisher Scientific Inc., Madison, WI, USA) equipped with a germanium Attenuated Total Reflection (ATR) accessory and a pressure tower.

Powder characterization: Physicochemical characterization was conducted on the sample IBU20, as a representation of the other milled samples, and the unmilled IBU by quantifying specific surface area (SSA), density, and angle of repose.

Brunauer-Emmett-Teller: Surface area (SA) was evaluated via a single-point BET method using a Monosorb® surface area analyzer (Quantrachrome Instruments; FL, USA) following 24 hour outgassing with helium at room temperature (RT) before each measurement in triplicate on a known powder mass (m). SSA was calculated using Equation 3:

$$SSA = \frac{SA}{m} \qquad \text{Equation (3)}$$

Helium pycnometry: True densities were measured using an MVP-D160-E multipycnometer (Quantrachrome Instruments; FL, USA) equipped with the micro cell and adapter. Measurements were conducted in triplicates. Before pressure measurements, the multipycnometer was purged with helium gas according to the manufacturer's recommendations.

Angle of repose: Angles of repose were measured in triplicate according to the United States Pharmacopoeia (USP) method. Images of the powder mounds were taken using a digital camera and were analyzed using the ImageJ software (Wayne Rasband, Research Services Branch, National Institute of Mental Health, Bethesda, MD, USA).

Bulk and tapped density: The bulk density ($\rho_B$) and tapped density ($\rho_T$) calculations were performed using a tapped density tester (Agilent Technologies, Santa Clara, CA, USA) for a small mass of powder using a modified USP method (USP General Chapter, 2015b). In this modified method, a 10 mL graduated cylinder fitted with a molded adapter substituted the 100 mL graduated cylinder in the tapped density tester. The compressibility index (CI) and Hausner ratio (HR) calculations were performed according to the following formulas:

$$CI = 100 \times \frac{\rho_T - \rho_B}{\rho_B} \qquad \text{Equation (4)}$$

$$HR = \frac{\rho_B}{\rho_T} \qquad \text{Equation (5)}$$

In vitro aerodynamic performance testing: For the in vitro aerodynamic performance testing, the DPI device was a high-resistance monodose RS01, a gift from Plastiape S.p.a. (Osnago, Italy). Vcaps No. 3 hydroxypropyl methylcellulose (HPMC) capsules were provided by Capsugel Inc. (Morristown, New Jersey, USA). The in vitro aerodynamic performance of carrier-free, high-dose DPI formulations were assessed using the Next Generation Impactor (NGI) (MSP Corporation, MN, USA) attached sequentially to a Whatman® HEPA filter (GE Healthcare Bio-Sciences, Pittsburgh, PA, USA), a volumetric digital flow meter (TSI 4000 Series, TSI Performance Measurement Tools, Shoreview, MN, USA), a two-way solenoid valve timer, and a high-capacity vacuum pump (HCP5, Copley Scientific Limited, Nottingham, UK).

For these studies, the DPI device was loaded with an HPMC capsule containing 10, 25, or 50 mg of IBU5 or 25 mg of IBU10.1, IBU10.2, or IBU20. Table 5 describes the formulations for in vitro aerodynamic performance studies.

TABLE 5

Dry powder inhaler capsule-fill weights and experimental conditions for 5, 10, and 20 g batches of jet-milled ibuprofen (IBU5, IBU10.1, IBU10.2, IBU20) for the in vitro aerodynamic performance analysis studies.

| Capsule-fill weight | 10 mg | 25 mg | 50 mg |
|---|---|---|---|
| IBU5 | 10IBU5 | 25IBU5 | 50IBU5 |
| IBU10.1 | — | 25IBU10.1, 25IBU10.1** 25IBU10.1', 25IBU10.1" | — |
| IBU10.2 | | 25IBU10.2, 25IBU10.2** | |
| IBU20 | — | 25IBU20, 25IBU20* | — |

*/**Formulations were stored in a desiccator under vacuum for 21 days (*), or 6 months (**) at room temperature (IBU10.1, IBU20), or at −80° C (IBU10.2).
'/"Formulations were purged with helium for 24 h at room temperature ('), or at 30° C. (").

Before testing, the preseparator was loaded with 15 mL of ethanol and the NGI stages were coated with silicon oil via application of 1% (v/v) of silicon oil in hexane. The temperature and relative humidity were measured using an SRH77A thermo-hygrometer by Cooper-Atkins Instrument Corporation (Middlefield, CT, USA). The in vitro aerodynamic performance of formulations were evaluated at a flow rate of 58.8 L/min creating a 4 kPa pressure drop across the DPI device for 4.08 s for a total volume of 4 L per Chapter 601 of the USP, apparatus 5 for inhalation powders in triplicates. The capsule, inhaler base, mouthpiece, adapter, induction port, preseparator, stages 1-7, and micro-orifice collector (MOC) were each washed twice with 5 mL of ethanol and their UV-absorbance were analyzed at the wavelength of 265 nm using a Tecan® Infinite® 200 PRO multimode microplate reader (Tecan Systems, Inc. San Jose, CA, USA).

Following the quantification of drug mass in each fraction, emitted dose percentage (ED) is defined as the percentage of the entire dose depositing downstream from the mouthpiece of the DPI where the entire dose is the total recovered drug mass in all the fractions. Respirable fraction percentage (RF) is defined as the percentage of the entire dose deposited on stages two through seven plus the MOC. Fine particle fraction percentage (FPF) is defined as the percentage of the emitted dose deposited on the stages two through seven plus the MOC. Fine particle (<5 μm) fraction percentage (FPF5 μm), fine particle (<3 μm) fraction percentage (FPF3 μm), and fine particle (<1 μm) fraction percentage (FPF1 μm) corresponded to the percentage of the emitted dose predicted to have the aerodynamic diameter below 5, 3, and 1 μm respectively. The FPF5 μm, FPF3 μm, and FPF1 μm values were interpolated from a graph with the cumulative percentage of the emitted dose deposited downstream from an NGI stage as the ordinate and the particle cutoff size of that stage as the abscissa.

PSD analysis by laser light diffraction: PSDs were determined using a Sympatec Helos equipped with a Cuvette module (System-Partikel-Technik GmbH, Clausthal-Zellerfeld, Germany). Data were analyzed using the Sympatec WINDOX software. For each measurement, per a previously optimized method, about 2 mg of powder was dispersed in 0.5 mL of 0.1% (w/v) sodium dodecyl sulfate in water and the sample was sonicated for 5 min. A reference measurement was performed on the cell filled with 50 mL of 0.005% (v/v) Tween 20 and 50 μL of 2.5 N hydrochloric acid in water. After the reference measurement, 50 μL aliquots of the sonicated suspension were added to the cell to achieve optical concentrations of between 10 to 20% and the total of six measurements were performed on each sample. Formulations immediately following air-jet milling (25IBU10.1, 25IBU10.2) and after 6 months (25IBU10.1, 25IBU10.2) stored at RT (IBU10.1), or at −80° C. (IBU10.2) were analyzed.

There were no detectable differences between IBU samples thermally and spectroscopically. The milled IBU sample exhibited improved powder flow in comparison with the unmilled sample. The milled IBU powders possessed surprisingly high in vitro aerodynamic performance with a fine particle fraction percentage between 67 and 85%, and a minimum respirable fraction percentage of 49%. The capsule-fill weights, from 10 to 50 mg, and milling batch sizes did not significantly influence performance. The importance of powder conditioning following milling was illustrated as the storage duration and temperature negatively affected performance.

Analysis of IBU samples (IBU5, IBU10.1, IBU10.2, and IBU20) using SEM showed that the samples were comprised of micronized particles with plate-like morphology as agglomerates of 10 to 30 μm. There were no morphological differences between the milled IBU batches.

XRD spectra from the samples of IBU5, IBU10.1, IBU10.2, and IBU20 overlapped and peaks corresponded closely with the peaks from the solved XRD diffractogram of racemic IBU, which is listed in Cambridge Structural Database (refcode: IBPRAC).

DSC thermograms for the sample IBU20 and unmilled IBU possessed endotherms at approximately 77.78° C. and 77.18° C. corresponding to the melting point of IBU. There were no other endotherms, exotherms, or phase transitions in the thermograms.

Peaks associated with the FT-IR spectra for the sample IBU20 and unmilled IBU overlapped. Sharp peaks at 1712.43 $cm^{-1}$ corresponded with the carbonyl group of the carboxylic acid functionality of the IBU molecule. The group of peaks surrounding 2955.20 cm-1 corresponded with the sp2 carbon-hydrogen bond stretches of the aromatic ring superimposed on the carboxylic acid oxygen-hydrogen bond stretch. Finally, 779.99 $cm^{-1}$ corresponds with para substitution on the aromatic ring of IBU.

Table 6 summarizes the powder characterization for the sample IBU20 and unmilled IBU.

TABLE 6

Sample characterization for the unmilled ibuprofen (IBU) and the 20 g batch of jet-milled ibuprofen (IBU20)

| Sample | SSA ($m^2$/g)[a] | ρ (g/$cm^3$)[a] | $\rho_B$ (g/$cm^3$) | $\rho_T$ (g/$cm^3$) | HR | CI | Angle of Repose (°)[a] |
|---|---|---|---|---|---|---|---|
| Unmilled IBU | 0.36 ± 0.01 | 1.14 ± 0.00 | 0.27 | 0.44 | 1.64 | 39.19 | 62.6 ± 2.9 |
| IBU20 | 2.02 ± 0.20 | 1.15 ± 0.01 | 0.12 | 0.21 | 1.82 | 45.00 | 37.8 ± 5.0 |

[a]N = 3, specific surface area (SSA), bulk density ($\rho_B$), tapped density ($\rho_T$), true density (ρ), compressibility index (CI) and Hausner ratio (HR)

There was a six-fold difference in SSA between the two samples (2.02 vs. 0.36 $m^2$/g); however, the true density measurements were the same. The calculated CI and HR based on the density measurements were as follows: 45.00 vs. 39.19 and 1.82 vs. 1.64. According to the USP, calculated CI greater than 25 and HR greater than 1.34 are indicative of poor flowability; however, the angle of repose improved from 62.6±2.9° for the unmilled IBU to 37.8±5° for the sample IBU20. IBU was transformed from a powder with almost very, very poor flow to one with almost good flow according to angle of repose testing.

Testing was conducted at relative humidity levels between 28 and 51% and RT of 23 and 25° C. Formulations 10IBU5, 25IBU5, and 50IBU5 performances were compared to evaluate the capsule-fill weight effect. Formulations 25IBU5, 25IBU10.1, 25IBU10.2, and IBU20 performances were compared to investigate the batch size effect. Capsule-fill weight and batch size did not significantly affect the performance. Formulations 25IBU20, 25IBU20*, 25IBU10.1, 25IBU10.1 performances were compared to evaluate the formulation performance effect on aging. Formulations 25IBU10.1, 25IBU10.1', and 25IBU10.1" performances were compared to evaluate the storage temperature effect. An increased storage duration and temperature affected the performance negatively. Finally, formulations 25IBU10.1, 25IBU10.1, 25IBU10.2, and 25IBU10.2** performances were compared to evaluate the storage temperature effect on aging. Decreased storage temperature was associated with improved performance.

The PSDs for formulations 25IBU10.1, 25IBU10.1, 25IBU10.2, and 25IBU10.2 were analyzed. The $D_{50}$ and $D_{90}$ values for the sample increased at RT after a six-month storage (2.19 & 4.23 μm vs. 3.00 & 13.23 μm). However, the $D_{50}$ and $D_{90}$ values for the sample did not change at −80° C. after a six-month storage (2.74 & 7.56 μm vs. 2.43 & 4.77 μm). The appearance of a secondary peak in the PSD after a six-month storage at RT was responsible for this increase.

The jet-milled samples possessed a plate-like morphology according to the SEM micrographs and were crystalline as determined by XRD. The crystalline structure corresponded with the conventional phase (phase I) of IBU. The DSC thermogram and FT-IR spectrum for sample IBU20, representative of all milled samples, corresponded to the thermogram and spectrum for the unmilled IBU. The melting point drop following air-jet milling, from 77.78 to 77.18° C., was due to the smaller particle size of the milled sample in comparison with the unmilled sample. Furthermore, the true density measurements by helium pyncometry matched literature-reported values.

Powder flow is critical in pharmaceutical processing including capsule filling for DPIs. Sample IBU20 showed an improved powder flow, signified by a smaller angle of repose, in comparison with the unmilled IBU (see Table 6). However, this observation was in contrast with the calculated CI and HR values and the notion that air-jet milling leads to poor powder flow due an increase in adhesive and cohesive forces where Van der Waals forces become greater than gravitational forces. As evident in SEM micrographs, the milled IBU particles formed agglomerates, which likely behaved as granules and resulted in a smaller angle of repose.

The SSA and the PSD parameters for sample IBU20 indicate formation of reversible agglomerates as opposed to irreversible agglomerates. The $D_{10}$, $D_{50}$, $D_{90}$ values for sample IBU20 were associated with individual particles, as agglomerates were disintegrated upon dispersion before sizing. Moreover, the theoretical particle size ($D_{theo}$=2.88 µm) was calculated based on SSA and ρ according to Equation 6.

$$D_{theo} = \frac{6}{SSA \times \rho} \qquad \text{Equation (6)}$$

The calculated $D_{theo}$ value for sample IBU20 corresponded to the measured $D_{50}$ value for the PSD, which implies the surface area for individual particles contributed to SSA. However, irreversible agglomerates would be associated with a smaller SSA and larger $D_{theo}$ value in comparison with reversible agglomerates. Moreover, superior in vitro aerodynamic performance data may imply that IBU particles form loose agglomerates.

ED values were found to be about 70% regardless of the capsule-fill weight. The RF values decreased slightly; however, the FPF values decreased when the capsule-fill weight increased from 10 to 50 mg. The observed drops were the most significant for the FPF1 µm value for formulation 50IBU5 with a relative drop of 25% in comparison with formulation 10IBU5. It has been previously shown that the monodose RS01 device resistance decreases with the increasing capsule-fill weight for the high resistance monodose RS01 device. Furthermore, a decreased device resistance is associated with a decreased deagglomeration efficiency at similar flow rates. The decreased RF and FPF values can be explained by the decreased degree of deagglomeration due to the resistance drop. Even though the performance was negatively affected by increasing capsule-fill weight, the decrease is not clinically significant since at least half of the dose per capsule can be delivered in practice.

A closer inspection of the breakdown of the deposition percentage for the different capsule-fill weights showed an increasing recovery percentage of the dose from the capsule walls with a decreasing capsule-fill weight; however, the recovered IBU mass was about 1 mg across all capsule-fill weights. Conversely, significantly larger IBU mass was recovered from the inhaler for 50IBU5 in comparison with 10IBU5 (27 vs. 20%, 14 vs. 2 mg). Accordingly, similar ED values were achieved for different capsule-fill weights. Furthermore, decreased FPF values were due to increased deposition levels in the induction port and the preseparator because of reduced deagglomeration efficiency with increasing capsule-fill weights.

The RF values for all formulations ranged from 49 to 55% and were not significantly different. Except formulation 25IBU10.2, the ED value remained at about 70% for other formulations (25IBU5, 25IBU10.1, 25IBU20); however, formulation 25IBU10.2 possessed the highest FPF values at 1, 3, and 5 µm. The deposition percentage breakdown showed the highest deposition in the capsule, inhaler base, mouthpiece, and stages four through seven and the lowest deposition in the induction port and preseparator for formulation 25IBU10.2. This deposition pattern implies that sample IBU10.2 contained the highest percentage of fine particles in comparison with the other milled samples. Fine particles adhere to the interior of the capsule, inhaler base, and mouthpiece; however, large particles are trapped in the induction port and preseparator during in vitro aerodynamic performance testing for DPI formulations.

There was a significant drop in the RF value from 52 to 43% for the formulation 25IBU20 immediately following air-jet milling and after a 21-day storage in a desiccator under vacuum at RT. Additionally, there was a similar drop in the RF value from 49 to 40% for formulation 25IBU10.1 immediately following air-jet milling and after a six-month storage at the same conditions. For both formulations, the ED values improved from 72 to 81%; however, the FPF, FPF5 µm, and FPF3 µm values dramatically dropped by 20% and the FPF1 µm values decreased by 50%. Specifically, the deposited IBU mass in the inhaler base and mouthpiece decreased, and the deposited IBU mass in the induction port and preseparator increased. This observation was attributed to IBU particle size growth and the formation of irreversible agglomerates within 21 days. However, there were no further changes from 21 days to six months of storage.

Upon storage at RT, a secondary peak upstream of the primary peak appeared in the PSD corresponding with the irreversible aggregates, which did not break apart upon dispersion before sizing. As it was previously discussed in the introduction, amorphous domains could be created during air-jet milling of crystalline material due to high energy input. Bridges could form between neighboring microparticles upon the crystallization of these domains and reversible agglomerates transform into irreversible agglomerates.

The in vitro aerodynamic performance following a 24-hour purge with helium at 30° C. versus RT yielded similar results, whereas an increased temperature accelerated this transformation to under 24 hours. The in vitro aerodynamic performance immediately after air-jet milling and after six months at −80° C. for formulation 25IBU10.2 was compared with the in vitro aerodynamic performance at RT for formulation 25IBU10.1. Sample storage at −80° C. limited the formation extent of irreversible aggregates and preserved the RF value at 51% following six-month storage. Furthermore, the secondary peak, corresponding with the irreversible aggregates, was absent in the PSD upon storage at −80° C. in comparison with storage at RT.

The in vitro aerodynamic performance data, following storage at RT and −80° C., suggest the need for a conditioning period immediately after air-jet milling and before further processing. The conditioning period could constitute, at least, a 21-day storage at RT, following which performance would stabilize after an initial drop. The performance following this conditioning period is acceptable since it is limited to a 20% relative drop and is superior in comparison with most commercial DPI formulations. Alternatively, the conditioning temperature could be reduced down to −80° C., during which the formation extent of irreversible aggregates is limited. However, this conditioning period is associated with an increased cost due to the temperature requirements.

The current study is the first report of in vitro aerodynamic performance data for a carrier-free, high-dose formulation of IBU. The RF values were at least about 50% for all formulations immediately after air-jet milling. Furthermore, with a minimum FPF3 µm and ED values of 55.8 and 72.6% for formulation 25IBU10.2, 40% of the dose is predicted to reach the deep lung with an aerodynamic diameter below 3 µm. These values are significantly larger than most commercial DPI formulations. To achieve the estimated maximum 300 mg/day dose requirement for CF via pulmonary delivery, based on an approximate maximum 3 g/day oral dose, six capsules with 50 mg capsule-fill weight are required to be administered every twelve hours assuming RF of 50%. Further experiments are warranted to evaluate other performance considerations (e.g. flow rate dependency, 2 kPa pressure drop, etc.) for the carrier-free, high-dose IBU formulation in combination with the high-resistance monodose RS01 inhaler.

The in vitro aerodynamic performances of the carrier-free, high-dose DPI formulations of IBU were tested for the first time. The formulations exhibited superior performance with predicted lung delivery of at least 40% of the dose regardless of capsule-fill weight, batch size and storage conditions. It is likely that some loose crystalline agglomerates in the carrier-free formulation transformed into irreversible agglomerates upon aging at RT within one month; however, there were no further changes by six months. This transformation is temperature dependent; it occurred within 24 hours at 30° C. and did not occur at −80° C. during a six-month period. Furthermore, the performance was minimally influenced by capsule-fill weight and batch size. In vitro aerodynamic performance of IBU is independent of capsule-fill weight and batch size; however, some period of powder conditioning is recommended to reduce variability in formulation performance.

Example 10

Optimization of air-jet milling conditions of ibuprofen (IBU) using the design of experiment (DoE) method were tested. Bulk IBU was micronized using an Aljet mill according to a circumscribed central composite (CCC) design developed in the JMP® statistical package, with grinding and pushing nozzle pressures varying from 20 to 110 psi. Output variables included yield and particle diameters at the $50^{th}$ and $90^{th}$ percentile. Following data analysis, the optimized conditions were identified and tested to produce IBU particles with the smallest particle size and acceptable yield. Finally, indomethacin (IND) was milled using the optimized conditions as well as the least favorable milling conditions as a control.

Successful deep lung deposition for dry powder inhaler (DPI) formulations, is strongly correlated to the percentage of particles with an aerodynamic diameter ($D_{ae}$) less than 3 µm. As depicted in Equation 7, for spherical, solid particles, the aerodynamic diameter is equal to the geometric diameter ($D_{eq}$) where particle density ($\rho_p$) is equal to unit density ($\rho_o$) and the dynamic shape factor ($\chi$) is equal to one.

$$D_{ae} = D_{eq} \sqrt{\frac{\rho_p}{\rho_o \chi}} \qquad \text{Equation (7)}$$

Microparticles with geometric diameters less than 3 µm can be produced via top-down approaches, such as an air-jet mill, as well as bottom-up approaches, such as a controlled crystallization method. Top-down approaches include: mechanical mills where the milling energy is imparted directly, fluid energy mills where the milling energy is imparted indirectly, and high-pressure homogenizers where the milling energy is imparted both directly and indirectly. An air-jet mill is an example of a fluid energy mill and is composed of a milling chamber where the powder is fed in through a hopper via a pushing nozzle, and particle collisions and fractures are caused by the introduction of one or more milling nozzles.

Fracture inducing mechanisms can be classified as impaction, compression, or attrition. During impaction and compression, the fracture inducing force is applied normal to the surface, leading to the formation of two or more fragments; however, it is applied parallel to the surface during attrition, and it results in the production of extremely fine particles. As opposed to the mechanical mills where impaction, compression, and attrition are all responsible for milling, in an air-jet mill only attrition is responsible for milling.

The extent of milling for a material is dependent on its mechanical properties, initial particle size distribution (PSD) and the milling conditions. If material experiences plastic deformation before fracture, it is classified as ductile; otherwise, it is classified as brittle. Brittle fracture is a function of temperature, strain rate, stress state, and particle size. The brittle-ductile transition occurs at the critical particle diameter, below which particles undergo a ductile fracture as opposed to a brittle fracture during milling, with an increased energy requirement. The critical diameter characterizing the brittle-ductile transition for ibuprofen (IBU) is reported as 854 µm and more recently between 125-355 µm, which makes milling IBU more difficult than other solids with smaller brittle-ductile transition critical diameters.

IBU, 2(4-isobutylphenyl)propanoic acid, has a molecular weight (MW) of 206.29 g/mol and is commercially available as a racemic mixture of S(+)-IBU (pharmacologically active) and R(−)-IBU (pharmacologically inactive). IBU exists either as the stable polymorph I with a melting point (MP) of 75.85° C., or as the less stable polymorph II, with a lower MP of 16.85° C. Previously, micronized IBU has been produced, and companies such as BASF have reported the minimum particle diameters at the $10^{th}$, $50^{th}$, and $90^{th}$ percentile ($D_{10}$, $D_{50}$, and $D_{90}$) at around 10, 25, 65 µm respectively. Furthermore, Shariare et al. reported air-jet milling of a <40 µm sieve fraction to a $D_{10}$, $D_{50}$, and $D_{90}$ of 0.75, 2.25, and 4.10 µm respectively where the starting particles were needle-shaped with a high degree of crystalline imperfection. Even though these materials may eventually be suitable for inhalation, multiple steps of crystallization, drying, sieving, and micronization were required to reach this PSD profile. In addition, the poor flowability of raw materials due to shape and their physical instability due to crystalline imperfections may not enable industrialization of such an approach. Alternatively, the optimization of milling such that appropriate particle sizes can be obtained using a single milling step is highly desirable and can be more easily commercialized.

Micronization of a bulk pharmaceutical grade of IBU via air-jet milling was investigated by application of a design of experiments (DoE) statistical method of optimization. Batch sizes were increased to evaluate effect of batch sizes on particle size distribution (PSD). Furthermore, optimized conditions for the micronization of indomethacin (IND), another non-steroidal anti-inflammatory drug with different physicochemical properties, were applied. It is believed that optimized conditions for the air-jet milling of IBU, a physically difficult material to micronize, could be used to mill IND with different physical and mechanical properties.

A Model 00 Jet-O-Mizer™ (also known as Aljet mill, Fluid Energy, Telford, PA) was configured according to FIG. 1, and it was used to micronize IBU and IND. For milling IBU, the milling conditions were varied between 20 and 110 psi for the pushing and grinding nozzle pressures. Throughout the DoE runs, the feed rate of 1 g/min and the batch size of 5 g were used. The milled powder samples were collected from the different segments of the jet mill in a desiccator under vacuum. The samples were from the segments illustrated in FIG. 1: (see also discussion in Example 11) the tube after grinding chamber (bfC), the cyclone (C), the collection vessel adapter (D), the collection bag adapter (E), the collection vessel (G), and the collection bag (H). Following powder collection, the yield percentage for each segment was calculated.

The DoE analysis results were used to predict the milling conditions allowing the maximum particle size reduction. For the scale-up experiments and testing the DoE predictions, the milling runs were conducted on IBU batch sizes of 5, 10, and 20 g using the optimized conditions from the DoE. Additionally, two 5 g batches of indomethacin (IND) were milled using the optimized conditions, as well as the worst milling conditions, as determined by the DoE.

Circumscribed central composite (CCC) experimental design with two center points was developed in JMP Pro 10 (SAS Institute Inc., Cary, North Carolina) statistical software. In a previous air-jet milling study, authors suggested to maximize attrition between particles, the grinding nozzle pressures could be set at the same pressure level. Therefore, both grinding nozzle pressures were grouped together as one variable, and along with the pushing nozzle pressure, were the two studied factors. With a CCC axial value of 1.414 for two factors and the initial factor values ranging between 35 and 95 psi, the experimental design runs were randomized and tabulated, and the factors' values were rounded to multiples of five. The values for grinding and pushing nozzle pressures ranged from 20 to 110 psi (Table 7).

TABLE 7

Circumscribed central composite experimental design with two center points

| Run # | Grinding Nozzle Pressure (psi) | Pushing nozzle Pressure (psi) |
|---|---|---|
| 1 | 110 | 65 |
| 2 | 65 | 110 |
| 3 | 35 | 95 |
| 4 | 65 | 20 |
| 5 | 35 | 35 |
| 6 | 95 | 95 |
| 7 | 65 | 65 |
| 8 | 20 | 65 |
| 9 | 65 | 65 |
| 10 | 95 | 35 |

The analyzed responses included: the yield, $D_{50}$, and $D_{90}$ values associated with the PSD for the recovered samples.

PSDs were determined using a Sympatec Helos equipped with a Cuvette module (System-Partikel-Technik GmbH, Clausthal-Zellerfeld, Germany). Data were analyzed using the Sympatec WINDOX software. For each measurement per a previously optimized method, about 2 mg of powder was dispersed in 0.5 mL of 0.1% (w/v) SLS in water and the sample was sonicated for 5 minutes. A reference measurement was performed on the cell filled with 50 mL of 0.005% (v/v) Tween 20 and 50 μL of 2.5 N HCl in water. After the reference measurement, 50 μL aliquots of the sonicated suspension were added to the cell to achieve optical concentrations of between 10 to 20% and the total of six measurements were performed on each sample. Analyzed samples included: unprocessed IBU and IND as well as the milled samples from different sections of the jet mill including the tube after grinding chamber (bfC), the cyclone (C), the collection vessel adapter (D), the collection bag adapter (E), the collection vessel (G) and the collection bag (H) for each run. The span value was calculated according to Equation 2.

To estimate the overall $D_{10}$, $D_{50}$, and $D_{90}$ values for the combined recovered fractions associated with each run, stacked bar charts were graphed and analyzed to determine the yield normalized cumulative PSDs. Each stacked bar corresponded to a particle size bin and its height corresponded to the volume density distributions' weighted averages by the yield for each segment of the jet mill. The $D_{10}$, $D_{50}$, and $D_{90}$ values for the normalized cumulative PSDs were the particle sizes corresponding to the 10, 50, and 90% area of the stacked bar chart respectively. This method was validated through the calculation of these values for a single PSD using this method and their comparison with the calculated values using the Sympatec WINDOX software.

Samples were mounted on standard aluminum SEM stubs, were sputter coated with 15 nm platinum/palladium (Pt/Pd) using a Cressington sputter coater 208 HR (Cressington Scientific Instruments Ltd., Watford, UK) and were imaged using a Zeiss Supra 40VP SEM (Carl Zeiss Microscopy GmbH, Jena, Germany).

The $4^{th}$ and $10^{th}$ runs were unsuccessful due to powder "blowback," where grinding nozzle pressures were significantly larger than the push nozzle pressure (65 vs. 20 psi and 95 vs. 35 psi). Due to the adhesion of IBU throughout the interior surface of the jet mill downstream from the milling chamber, milled samples from the different segments were collected individually. The overall yields ranged from 64.5 to 85.5% for the DoE runs. The percentage recovered in the collection bag ranged from 5.7 to 17.3%.

The primary goals of the DoE analysis were to minimize the $D_{50}$ and $D_{90}$ values of the PSDs and to maximize the yield percentage. Since the PSDs for the collection bag fraction were associated with the smallest $D_{50}$ and $D_{90}$ values, they were utilized for the DoE analysis. For the collection bag fraction, the $D_{50}$ values ranged from 3.2 to 11.9 μm, and the $D_{90}$ values ranged from 8.1 to 92.4 μm. Following the DoE analysis, it was determined that the grinding and pushing nozzle pressures have a significant effect on $D_{90}$ (p=0.0046*, 0.0090*) and the grinding nozzle pressure had a second-degree effect on $D_{90}$ (p=0.0064*). The $D_{50}$ and $D_{90}$ values for the yield normalized cumulative PSDs ranged from 6.4 to 12.5 μm for $D_{50}$ and 13.2 to 27.2 μm for $D_{90}$.

Figure 2:
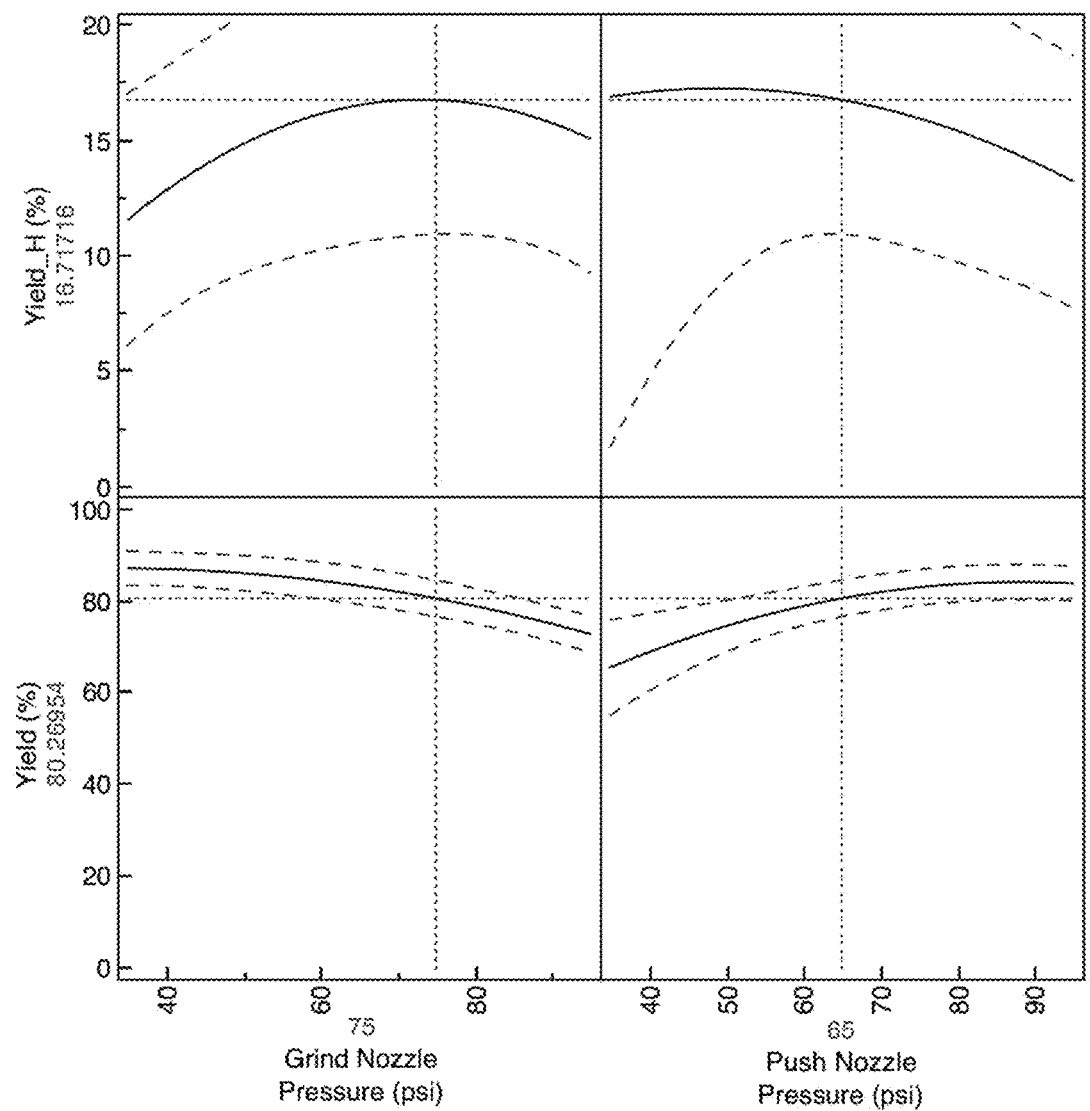
FIG. 2 is a graph illustrating a prediction profiler for an overall and a collection bag yield of a jet mill.
Figure 3:
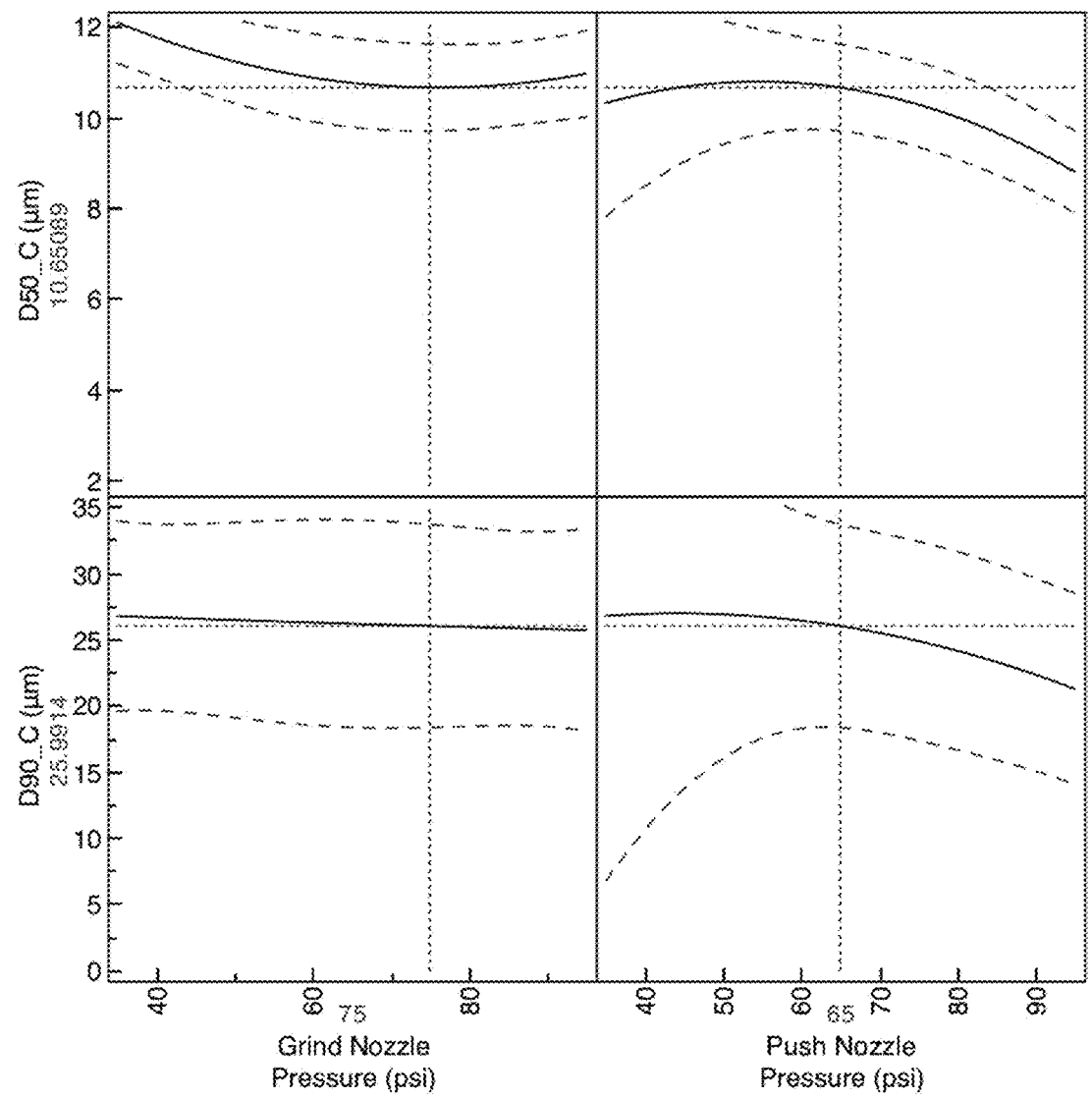
FIG. 3 is a graph illustrating a prediction profiler for a cyclone fraction yield of a jet mill.
Figure 4:
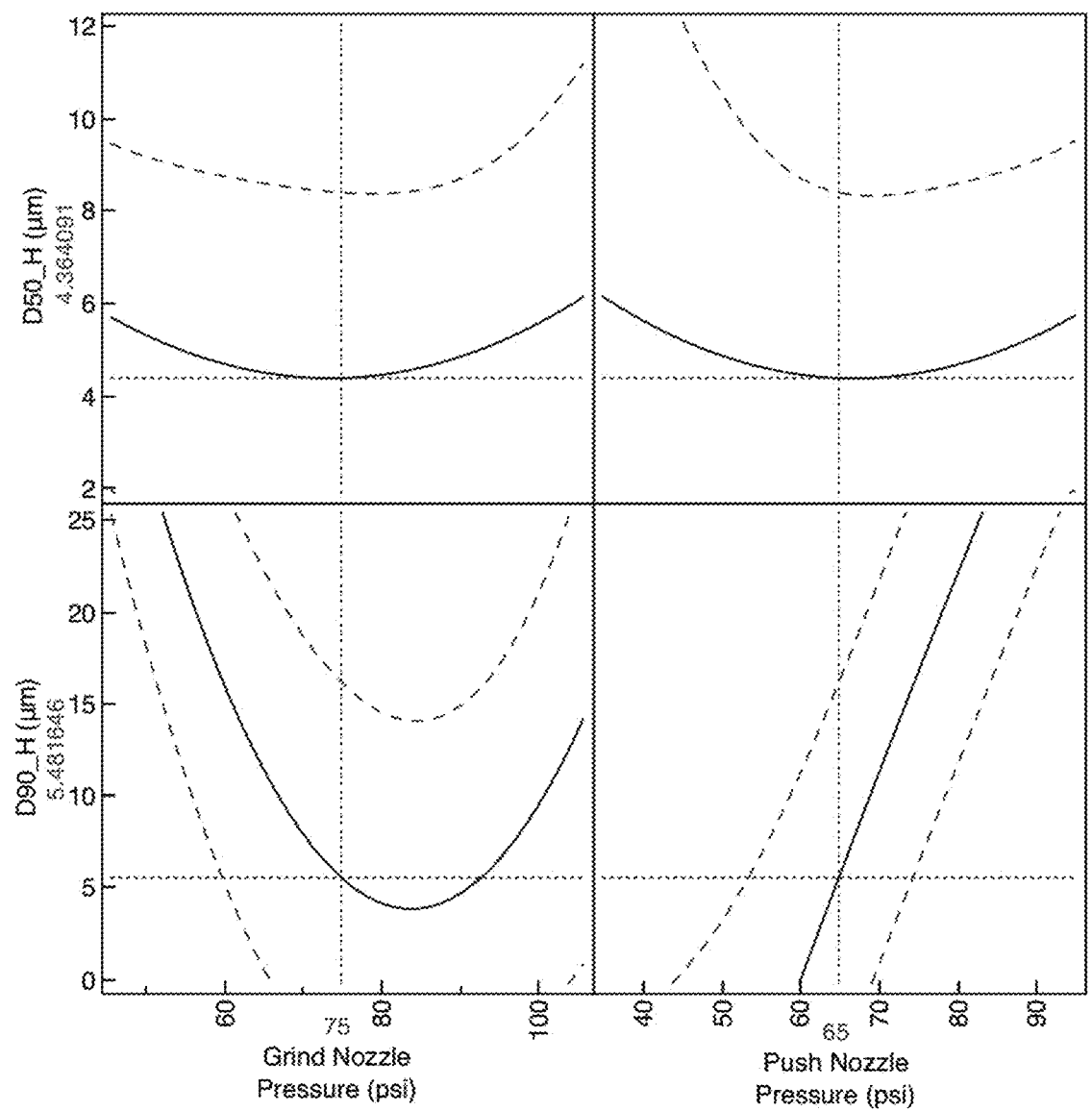
FIG. 4 is a graph illustrating a prediction profiler for a collection bag fraction yield of a jet mill.
Figure 5:
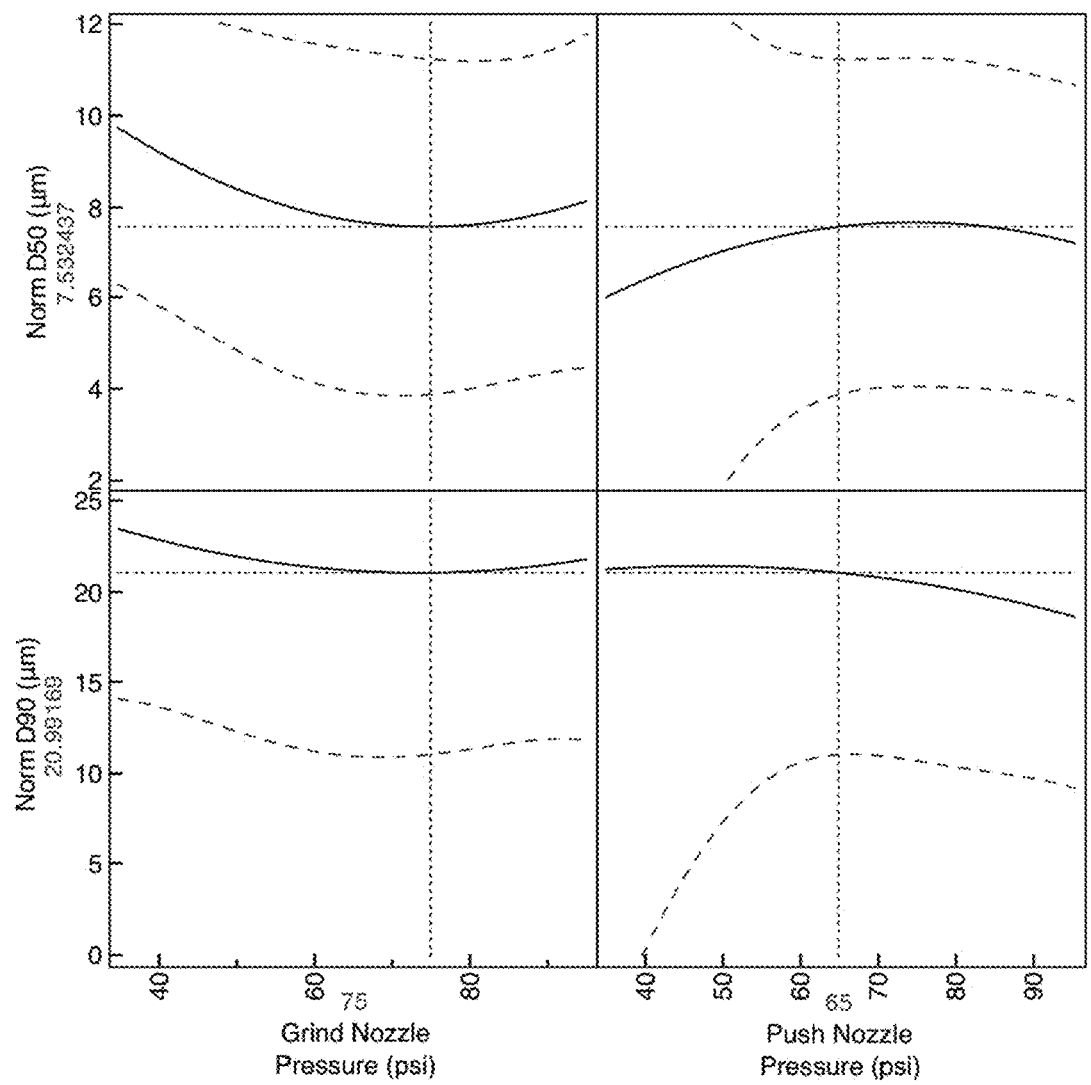
FIG. 5 is a graph illustrating a prediction profiler for a normalized cumulative yield of a jet mill.

Prediction profiler graphs were generated by JMP software (FIGS. 2-5) to predict the yield, $D_{50}$, and $D_{90}$ values as a function of the grinding and pushing nozzle pressures. To test the DoE analysis, the optimal yield and the PSD parameters were predicted for the grinding nozzle pressure of 75 psi and the pushing nozzle pressure of 65 psi. Specifically, FIG. 2 illustrates the prediction profiler for the overall and the collection bag yields. Likewise, FIGS. 3-5 illustrate the prediction profiler graphs for the $D_{50}$ and $D_{90}$ values for the PSDs associated with: the cyclone fraction (FIG. 3), the collection bag fraction (FIG. 4), and the yield normalized cumulative PSD (FIG. 5).

The DoE predictions were tested through milling a 5 g batch of IBU with a grinding nozzle pressure of 75 psi and a pushing nozzle pressure of 65 psi. Furthermore, milling was conducted on 10 and 20 g batches of IBU as well as 5 g batches of IND. The collection bag yield, $D_{50}$, $D_{90}$, and span values are presented in Table 8.

TABLE 8

The collection bag yield, the $D_{50}$, the $D_{90}$, and the span values for 5, 10, 20 g batches of the jet-milled ibuprofen (IBU) and indomethacin (IND)

| Name | GrindP (psi) | PushP (psi) | Yield (%) | $D_{50}$ (μm) | $D_{90}$ (μm) | Span |
|---|---|---|---|---|---|---|
| Stock IBU | — | — | — | 48.0 | 106.7 | 1.8 |
| IBU 5 g | 75 | 65 | 16.1 | 1.9 | 3.6 | 1.5 |
| IBU 10 g | 75 | 65 | 17.4 | 2.2 | 4.2 | 1.5 |
| IBU 20 g | 75 | 65 | 29.0 | 2.7 | 6.0 | 1.8 |
| Stock IND | — | — | — | 26.3 | 64.8 | 2.3 |
| IND+ 5 g | 75 | 65 | 2.3 | 1.2 | 2.7 | 1.7 |
| IND− 5 g | 35 | 35 | 2.7 | 1.8 | 4.4 | 2.1 |

The unprocessed IBU particles had a smooth acicular morphology with an approximate length of 150 μm and an approximate cross section of 20×20 μm. The milled IBU particles from the collection bag sizes ranged from 1 μm to greater than 5 μm with at least one smooth dimension and one or more rough dimensions. As opposed to the unprocessed IBU particles, the milled IBU particles existed as particle agglomerates of at least 20 to 30 μm.

The DoE method allowed for the IBU milling conditions optimization and led to a PSD with the $D_{50}$ and $D_{90}$ values significantly bellow the brittle-ductile transition critical diameter of IBU where dry milling below this size is more difficult. At the grinding nozzle pressure of 75 psi and the pushing nozzle pressure of 65 psi, the prediction profilers (see FIGS. 2-5) predicted the maximal yield for the collection bag fraction, the smallest $D_{50}$ value for the cyclone and the collection bag fraction PSD, and the smallest $D_{50}$ and $D_{90}$ value for the yield normalized cumulative PSD. The collection bag and the overall yields from the DoE testing experiment corresponded closely with the yields predicted by the prediction profilers. On the other hand, the $D_{50}$ and $D_{90}$ values for the collection bag fraction from the DoE testing experiment were less than the $D_{50}$ and $D_{90}$ values predicted by the prediction profiler (see Table 8, 1.9 vs. 4.36 μm and 3.6 vs. 5.48 μm). As depicted in Table 8, the collection bag fraction $D_{50}$ and $D_{90}$ values increased with increasing batch sizes. The $D_{50}$ and $D_{90}$ values for the 20 g batch agreed more closely with the predicted values using the prediction profiler. Batch size independent processing conditions are advantageous during scale up in the pharmaceutical industry.

During milling using the optimized conditions, the collection jar and the collection bag fractions had a left-shifted PSD in comparison with the other fractions. This shift is responsible for the formation of a bimodal distribution in the yield normalized cumulative PSD. Fine IBU aggregates deposition in the collection jar versus fine IBU particles deposition in the collection bag could explain similar PSDs for these two fractions. In contrast with the $D_{90}$ values of the collection bag fractions, the yield normalized cumulative PSDs $D_{90}$ values did not exceed 30 μm. Since the collection bag fraction yields are about 10%, the larger particles effects on the yield normalized cumulative PSDs $D_{90}$ values become smaller.

For each DoE run, a pressure index (PI) value was calculated using Equation 8, where $P_0$ was set to 1 psi; these values are tabulated in Table 9.

$$\text{Pressure Index} = \log \frac{\text{Grinding nozzle pressure}^2}{\text{Pushing nozzle pressure} \cdot P_0} \quad \text{Equation (8)}$$

TABLE 9

The Circumscribed central composite experimental design with two center points with the Pressure Index (PI) calculation for each run where PI = log (Grinding nozzle pressure²/Pushing nozzle pressure × $P_0$), and $P_0$ = 1 psi.

| Run # | Grinding Nozzle Pressure (psi) | Pushing nozzle Pressure (psi) | PI |
|---|---|---|---|
| 1 | 110 | 65 | 2.27 |
| 2 | 65 | 110 | 1.58 |
| 3 | 35 | 95 | 1.11 |
| 4 | 65 | 20 | 2.32 |
| 5 | 35 | 35 | 1.54 |
| 6 | 95 | 95 | 1.98 |
| 7 | 65 | 65 | 1.81 |
| 8 | 20 | 65 | 0.79 |
| 9 | 65 | 65 | 1.81 |
| 10 | 95 | 35 | 2.41 |

There was a good correlation ($R^2$=0.83) between the cyclone yield and the PI values. A decrease in the PI value was associated with an increase in the flow level through the cyclone, thereby increasing the likelihood to impact and to trap the largest particles on the cyclone wall. The two largest PI values (2.32 & 2.41) were associated with the 4$^{th}$ and 10$^{th}$ runs (see Table 9), which were terminated due to powder blowback. These PI values were followed by the PI value for the 1$^{st}$ run (2.27), which was conducted successfully. Accordingly, the powder blowback inducing PI value lies between 2.27 and 2.32.

Furthermore, there was a good correlation ($R^2$=0.71) between the collection bag fraction $D_{90}$ and the PI values. Previously, it was reported that the pushing nozzle pressure does not influence the particle size as significantly as the grinding nozzle pressure. Low grinding and high pushing nozzle pressures correspond with low PI values and were associated with the collection bag $D_{90}$ values close to the unprocessed material. Decreasing the grinding nozzle pressure reduced the frequencies of the particle-particle and the particle-wall collisions and decreased the milling efficiency. Moreover, an increase in the pushing nozzle pressure is associated with a less efficient particle size reduction caused by a shorter sample residence time in the grinding chamber.

The overall yields for the DoE runs were greater than 80% except for the first run. However, the collection bag yield was greater than 15% only for the central points. Increasing batch sizes from 5 to 20 g improved the yield from 16.1 to 29% (see Table 8). Low recovery yields from the collection bag are permissible since IBU is a low-cost API. Besides, bulk IBU with different starting particle sizes and double milling could be used to increase the collection bag yield.

In comparison with the IBU milling using the optimized conditions, the IND milling yielded smaller particles, where the $D_{90}$ value was less than 3 µm and the $D_{50}$ value was about 1 µm. Moreover, the least favorable milling conditions based on the DoE led to the micronization of IND; however, the micronization was not as efficient as the optimized conditions and the PSD possessed a larger span. IND would less likely undergo the ductile mode of fracture due to a higher strength of crystal lattice than IBU with an MP of 158° C., which is almost twice the MP for IBU. Furthermore, IND has a more brittle crystalline structure than IBU since it underwent a higher degree of comminution than IBU. This observation is supported by a smaller predicted brittle-ductile transition critical diameter for IND in comparison with IBU. At particle sizes above this diameter, IND undergoes the brittle mode of fracture, whereas IBU undergoes the ductile mode of fracture. However, the smaller initial $D_{50}$ and $D_{90}$ values for IND could be a contributory factor for the smaller final $D_{50}$ and $D_{90}$ values for IND in comparison with IBU.

CCC design included eight successful runs for milling IBU out of the ten total runs. The two failed runs were associated with powder "blowback" from the feed hopper due to a mismatch between the pushing and grinding nozzle pressures. From the completed runs, interpolation was performed to identify the optimized conditions. In subsequent validation experiments using these conditions, the experimental output values corresponded closely with the DoE modeling predicted values. The optimized conditions were superior to the control conditions for the micronization of IND.

A single-step air-jet milling process led to the successful comminution of IBU, a material with a high brittle-ductile transition particle diameter, and the optimized milling conditions could also be successfully used for the micronization of IND. Being a soft solid with a low MP, IBU has a large brittle-ductile transition critical diameter. IBU showed to be a good model drug for the optimization of a single-step air-jet milling. The DoE method allowed for the optimization of the milling conditions, which were used for the micronization of IBU and IND. Furthermore, the calculated PI values predicted failed runs as well as particle trapping in the cyclone for the Aljet mill. Increasing IBU batch sizes improved the collection bag fraction yield with the relative preservation of PSD. In future studies, the in vitro aerodynamic performance and the stability of the micronized IBU will be investigated to develop a carrier-free, high-dose DPI formulation with the potential to reach the deep lung regions upon successful aerosolization.

Example 11

A study was conducted to combine the benefits of hollow, low-density particles with the advantages of needle-shaped particles for the development of a high dose, carrier-free formulation of DF. It is believed that hollow needle particles of DF with a high aspect ratio would have a comparable in vitro aerodynamic performance to micronized particles of DF and DFNa. The particle morphology of DF in the forms of DF free acid and DFNa salt, as a carrier-free DPI formulation for lung delivery, was researched. DF was prepared from DFNa utilizing the pH-dependent aqueous solubility of DF. Micronized formulations were produced via the jet milling of DF and DFNa, and their in vitro aerodynamic performances were evaluated using a Next Generation Impactor (NGI).

DF-free acid was formed from DFNa. For DF free acid formation experiments, hydrochloric acid (HCl) was purchased from Fisher Scientific (Pittsburgh, PA, USA) and the house $dH_2O$ was used for preparing the solutions. A solution of 5.376 g of DFNa (Letco Medical, Decatur, Alabama, USA) was prepared in 1 L $dH_2O$ to get a 0.5% (w/v) concentration of DF in water. Using a burette, 2.5 N aqueous HCl was added to the DFNa solution dropwise, and the solution pH was obtained using an Accumet1 Basic AB/15+ (Fisher Scientific, Pittsburgh, PA, USA). Titration of the conjugate base of DF was continued until the solution reached a pH of 2.0. The precipitate was vacuum filtered and was dried overnight in a 40° C. oven.

Model 00 Jet-O-Mizer™ (also known as Aljet mill, Fluid Energy, Telford, PA, USA) was used to micronize DF and DFNa. Aljet mill was configured according to the schematic shown in FIG. 1. Jet milling parameters were optimized in unpublished work and were previously disclosed in a patent application pertaining to carrier-free high-dose formulations of non-steroidal anti-inflammatory agents. The jet milling parameters are as follows: the feed pressure of 65 psi, the grind pressure of 75 psi, the feed rate of 1 g/min, and the batch size of 5 g. Jet-milled powder samples were collected in scintillation vials and were stored in a desiccator under vacuum from different sections of the jet mill including: the tube after grinding chamber (bfC), the cyclone (C), the collection vessel adapter (D), the collection bag adapter (E), the collection vessel (G), and the collection bag (H). Following powder collection and weighing of scintillation vials with known tare weights, total yield, and individual recovery percentages were calculated. Temperature and relative humidity were measured using a SRH77A thermo-hygrometer by Cooper-Atkins Instrument Corporation (Middlefield, CT, USA).

Samples were mounted on standard aluminum SEM stubs, were sputter coated with 15 nm platinum/palladium (Pt/Pd) using a Cressington sputter coater 208HR (Cressington Scientific Instruments Ltd., Watford, UK) and were imaged using a Zeiss Supra 40VP SEM (Carl Zeiss Microscopy GmbH, Jena, Germany).

PSDs of DF and DFNa samples from the bfC, C, D, E, G, and H segments were analyzed before and after jet milling using a Sympatec HELOS, equipped with a CUVETTE module (System-Partikel-Technik GmbH, Clausthal-Zellerfeld, Germany). Tween 20 and sodium lauryl sulfate (SLS) were purchased from Fisher Scientific (Fisher Scientific, Pittsburgh, PA, USA), and dH2O was used for preparing solutions. For DF, about 2 mg of DF was dispersed in 0.5 mL of 0.1% (w/v) SLS in water and the sample was sonicated for 5 min. Reference measurement was done on acidified 50 mL of 0.005% (v/v) Tween 20 in water with 50 mL of 2.5 N HCl in water. For DFNa, about 2 mg of DFNa was dispersed in 0.5 mL of 0.1% (v/v) Span 85 in light mineral oil and the dispersion was sonicated for 5 min. A reference measurement was done in 0.1% (v/v) Span 85 in light mineral oil. After a reference measurement, aliquots of 50 mL of sonicated suspension were added to achieve optical concentrations from 10 to 20% for a total of six measurements.

Furthermore, $D_{10}$, $D_{50}$, and $D_{90}$ values for each sample were defined as particle diameters at the 10th, 50th, and 90th percentile of the PSD. Span was calculated according to Equation 2. Normalized cumulative PSDs were composed of yield-normalized distributions, where they were depicted as stacked bar charts. $D_{10}$, $D_{50}$, and $D_{90}$ values for normalized cumulative PSDs were calculated by approximating particle sizes associated with 10%, 50%, and 90% area of the stacked bar chart. The approximated values from this method were validated with the $D_{10}$, $D_{50}$, and $D_{90}$ values for a single distribution by the Sympatec software.

Thermograms were obtained using an Auto Q20 (TA Instruments-Waters LLC, New Castle, DE, USA) differential scanning calorimeter (DSC) controlled by TA Advantage Software (TA Instruments-Waters LLC, New Castle, DE, USA) and equipped with a RCS40 (TA Instruments-Waters LLC, New Castle, DE, USA) refrigerated cooling system with nitrogen purge of 50 mL/min. About 4 mg of samples were loaded in standard DSC pans (DSC Consumables Inc., Austin, MN, USA) and were crimped using a Tzero sample press (TA Instruments-Waters LLC, New Castle, DE, USA). Samples were heated at the rate of 10 C/min from 30° C. to 300° C.

FT-IR spectra were obtained using a Nicolet™ iSTM50 FT-IR Spectrometer (Thermo Fisher Scientific Inc., Madison, WI, USA) equipped with a germanium Attenuated Total Reflection (ATR) accessory and a pressure tower for the unprocessed and jet-milled powder.

Two-dimensional X-Ray diffractograms of DF and DFNa before jet milling were obtained using an automatic R-Axis Spider (Rigaku Corporation, Tokyo, Japan), an X-ray single crystal diffractometer controlled by RINT Rapid software with the target radiation of Copper at 40 KV voltage and 40 mA current. Samples for analysis were suspended in light mineral oil and were loaded on loops epoxied to conventional goniometer bases. Additionally, a background X-Ray diffractogram of light mineral oil loaded on a loop was subtracted from the samples' diffractograms, one-dimensional 2 u diffractograms were generated, and .txt files were saved using 2DP Software (Ragaku Corporation, Tokyo, Japan). To analyze the one-dimensional diffractograms using Jade (Ragaku Corporation, Tokyo, Japan), .raw files were generated from .txt files using ConvX.exe (Mark Bowden, Industrial Research Ltd., Lower Hutt, New Zealand).

Brunauer-Emmett-Teller (BET) specific surface area (SSA) measurements were taken. Surface area (SA) was evaluated via a single-point BET method using a Monosorb® surface area analyzer (Quantrachrome Instruments; FL, USA) following 24 hour outgassing with helium at room temperature before each measurement in triplicates. Samples masses (m) were at least 50 mg for the jet-milled powders depending on availability and 500 mg for the unprocessed samples. SSA was calculated according to the following formula:

$$SSA = \frac{SA}{m} \qquad \text{Equation (9)}$$

True densities were measured using a MVP-D160-E multipycnometer (Quantrachrome Instruments; FL, USA). For density measurements, the micro cell and the micro cell adapter were used, and samples weighed at least 0.1 g for the jet-milled powders depending on availability and at least 0.6 g for the unprocessed powders.

The angle of repose measurements were done triplicate according to the United States Pharmacopoeia (USP) method. Images of the powder mounds were taken using a digital camera and were analyzed using the ImageJ software (Wayne Rasband, Research Services Branch, National Institute of Mental Health, Bethesda, MD, USA).

The tapped density (rT) calculations were performed using a tapped density tester (Agilent Technologies, Santa Clara, CA, USA) with a modified method from the USP for a small mass of powder. In this modified method, a 10 mL graduated cylinder fitted with a molded adapter substituted the 100 mL graduated cylinder for the calculations of the bulk density (rB) and the use in the tapped density tester. The compressibility index (CI) and the Hausner ratio (HR) calculations were performed according to the following formulas:

$$CI = 100 \times \frac{\rho_T - \rho_B}{\rho_B} \qquad \text{Equation (10)}$$

$$HR = \frac{\rho_B}{\rho_T} \qquad \text{Equation (11)}$$

Karl-Fischer moisture analysis was performed. The moisture content of the unprocessed and jet-milled powders were measured in triplicates using a Photovolt Aqua-test™ 2010a Moisture Analyser (a.k.a. The CSC Aquapal III, CSC Scientific Inc., Fairfax, VA, USA). Powder moisture contents were calculated by subtracting the moisture content in 1 mL of anhydrous methanol (Fisher Scientific, Pittsburgh, PA, USA) from the moisture content reading from 5 mg powder dissolved in 1 mL of anhydrous methanol.

Ultraviolet absorbance was measured using a Tecan1 Infinite1 200 PRO multimode microplate reader (Tecan Systems, Inc. San Jose, CA, USA) using either a cuvette or Costar® Corning® 96-well UV-transparent plate. Ultraviolet-visible absorbance scans were performed at wavelengths from 230 to 1000 nm at the resolution of 2 nm. Additionally, absorbance scans were performed at similar ranges for an ethanol blank, and absorbance differences were plotted against the wavelength and in the Microsoft Excel®. Standard concentration curves were prepared for DF and DFNa. Wavelength with maximum absorbance was used for such measurements. Regression lines were forced through zero, and the R2 values were evaluated.

For the in vitro aerodynamic performance testing, the DPI device was a high resistance monodose RSO1, a generous gift from Plastiape S.p.a., (Osnago, Italy). Vcaps No. 3 HPMC capsules were generous donations from Capsugel Inc. (Morristown, New Jersey, USA). In vitro aerodynamic performance of the jet-milled powders were assessed using the NGI (MSP Corporation, MN, USA) attached sequentially to a Whatman® HEPA filter (GE Healthcare Bio-Sciences, Pittsburgh, PA, USA), a volumetric digital flow meter (TSI 4000 Series, TSI Performance Measurement Tools, Shoreview, MN, USA), a two-way solenoid valve timer box, and a high capacity vacuum pump (HCP5, Copley Scientific Limited, Nottingham, UK). For these studies, a high-resistance Monodose RSO1 DPI device was loaded with an HPMC capsule containing 10 mg of micronized powder. Prior to impactions, the pre-separator was loaded with 15 mL of ethanol and the NGI stages were coated with 5 mL of 1% (v/v) of silicon oil in hexane and a silicon oil coat was formed on the stages with hexane evaporation. Furthermore, the device resistance was calculated using a dosage unit sampling apparatus according to an abbreviated Apparatus B from the USP Chapter 601 and based on the calculated device resistance, flow rate creating a 4 kPa pressure drop across the DPI was calculated. Temperature and relative humidity were measured using an SRH77A thermo-hygrometer by Cooper-Atkins Instrument Corporation (Middlefield, CT, USA). In vitro aerodynamic performance of carrier-free formulations were evaluated at the Calculated flow rate for a total volume of 4 L per the USP Chapter 601, Apparatus 5 for Inhalation Powders in triplicates. The DPI capsule, the inhaler base, the mouthpiece, and the adapter were each washed twice with 5 mL of ethanol, and the 10 mL washes from each were stored in 15 mL centrifuge tubes for quantitative sample analysis. Accordingly, the induction port, the stages 1-7, and the micro-orifice collector (MOC) were each washed twice with 5 mL of ethanol and the 10 mL washes were collected as described. Finally, the pre-separator was washed with 10 mL of ethanol, and a total of 25 mL wash was collected.

Following the quantification of the drug mass in each fraction, the emitted dose percentage (ED %) is defined as the percentage of the entire dose depositing downstream from the mouthpiece of the DPI where the entire dose is the total recovered drug mass in all the fractions. The respirable fraction percentage (RF %) is defined as the percentage of the entire dose deposited on stages two through seven plus the MOC. The fine particle fraction percentage (FPF %) is defined as the percentage of the emitted dose deposited on the stages two through seven plus the MOC. Fine particle fraction (<5 μm) percentage (FPF5 μm %), fine particle fraction (<3 μm) percentage (FPF3 μm %), and fine particle fraction (<1 μm) percentage (FPF1pm %) are calculated from the cumulative percentage of the emitted dose deposited downstream of the NGI stage versus the particle cutoff size of the stage graph and correspond to the percentages of the emitted dose predicted to have the aerodynamic diameter below 5, 3, and 1 μm respectively.

TABLE 10

Recovery percentages from different sections of the jet mill including: tube after grinding chamber (bfC), cyclone (C), collection vessel adapter (D), collection bag adapter (E), collection vessel (G), and collection bag (H) for 5 g batches of diclofenac sodium and diclofenac.

| | Beck | C | D | E | G | H |
|---|---|---|---|---|---|---|
| Diclofenac sodium | 8.7 | 23.9 | 11.5 | 0.8 | 11.1 | 14.6 |
| Diclofenac | 8.0 | 33.6 | 9.4 | 0.4 | 6.5 | 5.6 |

Formation of DF free acid from DFNa was observed. With the addition of less than 1 mL of 2.5 N HCl to the aqueous solution of DFNa, a white precipitate of DF was formed. Vacuum filtration and overnight drying in the oven yielded a soft cake of white powder. Physicochemical characterization confirmed the presence of the DF free acid.

Jet milling of DF and DFNa was conducted at relative humidity levels between 48 and 55% and temperatures of around 24° C. Following the jet milling of 5 g batches, recovery percentages from various sections of the jet mill were determined and are shown in Table 10. There was a 70.6% total recovery associated with DFNa and a 63.6% total recovery associated with DF, with the majority of particles deposited in the primary cyclone. When comparing DF and DFNa deposition on the different components of the jet mill, there were noticeable differences in the recovery percentage from the cyclone, the collection vessel, and the collection bag.

SEM analysis showed that unprocessed DFNa was composed of relatively irregularly shaped particles with surface adhered fine particles. Precipitated DF particles were hollow needles with smooth surfaces and cross-sections below 5 μm, thicknesses of 0.5 pim and an average length of 20 μm. The jet-milled DFNa and DF particles were more similar concerning their PSD, as they both were composed of fine particles no larger than 3 μm. However, the jet-milled DF particles had a smoother surface than the jet-milled DFNa particles.

PSD analysis showed that powders collected from different sections of the jet mill were associated with different PSD. In Table 12, $D_{10}$, $D_{50}$, $D_{90}$, and span values are compared for: the normalized cumulative particle size distribution of jet-milled DFNa versus DF, unprocessed DFNa versus DF, as well as the collection bag fraction of jet-milled DFNa versus the cyclone fraction of jet-milled DF.

TABLE 12

$D_{10}$, $D_{50}$, $D_{90}$, and span associated with relevant samples of diclofenac sodium (DFNa) vs. diclofenac (DF).

| | DFNa vs. DF | $D_{10}$ (μm) | $D_{50}$ (μm) | $D_{90}$ (μm) | Span |
|---|---|---|---|---|---|
| Normalized cumulative particle size distribution of jet-milled DFNa vs. DF | DFNa | 1.29 | 3.25 | 6.53 | 1.61 |
| | DF | 1.16 | 2.36 | 4.48 | 1.41 |
| Unprocessed DFNa vs. DF | DFNa | 2.02 | 19.5 | 42.69 | 2.08 |
| | DF | 2.00 | 6.98 | 17.34 | 2.20 |
| Collection bag from jet-milled DFNa vs. cyclone from jet-milled DF | DFNa | 1.06 | 2.72 | 5.52 | 1.64 |
| | DF | 1.31 | 2.61 | 4.73 | 1.31 |

The $D_{50}$ and span values (2.36 μm and 1.41) associated with the cumulative particle size distribution for jet-milled DF were smaller than the $D_{50}$ and span values (3.25 μm and 1.61) for jet-milled DFNa. Due to the comparable median particle size for the collection bag fraction from the jet milling of DFNa, and the cyclone fraction from the jet milling of DF (2.72 μm vs. 2.61 μm), these fractions were chosen for further characterization and in vitro performance analysis, and will be referred as jet-milled DFNa and jet-milled DF hereinafter.

DSC thermograms of the DFNa and the jet-milled DFNa powders possessed two endotherms at 286.66° C. and 293.88° C. DSC thermograms of the DF and the jet-milled DF powder possess a single endotherm at 181.73° C., corresponding to the melting point of DF.

Peaks associated with the FT-IR spectra of DF and jet-milled DF, as well as DFNa and jet-milled DFNa, overlapped. In the DFNa spectrum, the 1557.57 cm-1 and the 1574.88 cm$^{-1}$ peaks were associated with the carboxylate group stretching; however, the 1690.81 cm$^{-1}$ peak in the DF spectrum was associated with a carboxylic acid stretching. Furthermore, the DF spectrum contained a 938.39 cm-1 peak corresponding to the O—H bending and the ~3320 cm$^{-1}$ peak associated with the O—H stretching, both absent in DFNa spectrum.

Background subtracted X-ray diffractograms for DF and DFNa were associated with different peaks and did not overlap.

Table 13 summarizes the bulk, the tapped, and the true density as well as the BET SSA, the angle of repose, and the moisture content determined by Karl-Fischer titration.

TABLE 13

Summary table of powder characterization

| Sample | SSA(m²/g)* | Moisture content (%)* | ρ(g/cm³)* | $\rho_\beta$(g/cm³)* | $\rho_T$(g/cm³) | HR | CI | Angle of Repose (°)* |
|---|---|---|---|---|---|---|---|---|
| DF | 1.73 ± 0.18 | 0.78 ± 0.18 | 1.48 ± 0.01 | 0.16 | 0.30 | 1.88 | 46.67 | 34.5 ± 2.3 |
| Jet-milled DF | 2.40 ± 0.21 | 0.45 ± 0.10 | 1.53 ± 0.18 | 0.12 | 0.26 | 2.08 | 51.85 | 31.2 ± 1.2 |
| DFNa | 1.37 ± 0.20 | 1.88 ± 0.20 | 1.51 ± 0.00 | 0.38 | 0.69 | 1.83 | 45.24 | 48.7 ± 5.5 |
| Jet-milled DFNa | 11.3 ± 0.81 | 2.99 ± 0.10 | 1.68 ± 0.04 | 0.17 | 0.20 | 1.22 | 18.18 | 26.3 ± 1.7 |

*N = 3, specific surface area (SSA), bulk density (rB), tapped density (rT), true density (r), compressibility index (CI) and Hausner ratio (HR).

Following jet milling, HR and CI calculations of flow showed no significant changes in flow for DF (1.88 and 46.67 vs. 2.08 and 51.85); however, they showed improved flow from very, very poor to fair flow for DFNa (1.83 and 45.24 vs. 1.22 and 18.18). The angle of repose improved from 48.7±5.5 to 26.3±1.7 following jet milling for DFNa, improving the flow property of the powder from poor to excellent according to the USP. On the other hand, the angle of repose remained good according to the USP classification (34.5±2.3 vs. 31.2±1.2) following jet milling for DF.

In vitro aerodynamic performance testing was performed. Device resistance calculations have been performed previously on a high-resistance Monodose RSO1 DPI for the device alone and the device loaded with an empty capsule and 10 mg powder mass. Device resistances were measured at 0.0393, 0.0348, 0.0347 kPa 0.5× min/L. The resistance of 0.034 kPa0.5× min/L was used to calculate the flow rate of 58.8 L/min that creates a 4 kPa pressure drop. Duration of 4.08 seconds at the flow rate of 58.8 L/min corresponded to 4 L air required per the USP for the in vitro testing of formulations and inhalers. In vitro aerodynamic performance NGI testing was conducted at relative humidity and temperature of 52% and 24° C. for jet-milled DFNa; 41% and 23.7° C. for jet-milled DF; and 40% and 24° C. for DF. The quantitative sample analysis of DF and DFNa were performed at the maximum UV absorbance of 282 nm for DFNa and the maximum UV absorbance of 278 nm for DF. Deposition percentages of the total dose for the different stages of the NGI were graphed and key parameters for performance evaluation are shown in Table 14.

SEM revealed the tubular (i.e. hollow acicular, hollow needle) crystal habit of DF free acid. Previously, Beck et al. employed a similar technique to prepare the free acid of DF; however, following precipitation, DF was recrystallized from a 1:1 ethanol/water solution. To the best of our knowledge, the current study is the first report on DF crystals with hollow needle morphology and the first report for the formation of these crystals using a single solvent system where tubular crystals are formed only by changing ph. There are other reports of this crystal habit in the literature for other drug substances. Eddleston and Jones reported the conditions required for the formation of tubular crystal habit for caffeine, carbamazepine, carbamazepine dihydrate and theophylline monohydrate. The formation of the cavities is attributed to the diffusion limited conditions at the center of the growing needle crystal. It has been found that crystal growth occurs more quickly than the diffusion of molecules to the quickest growing face of the crystal.

The DSC, the FT-IR, and the XRD data confirmed the identity of DF free acid. The results showed that the DSC thermogram of DFNa possesses two endotherms at 286.66° C. and 293.88° C., which correspond to a literature value of 284.3° C. On the other hand, the DSC thermogram of DF possessed a single endotherm at 181.73° C. with no evidence of DFNa endotherm corresponding to the reported melting point of DF. In the FT-IR spectrum of DFNa, the 1557.57 cm⁻1 and the 1574.88 cm⁻1 peaks are associated with the carboxylate group stretching; however, the 1690.81 cm⁻1 peak in the DF spectrum is associated with the carboxylic acid stretching. Furthermore, DF spectrum is associated with

TABLE 14

Summary table of in vitro aerodynamic performance parameters for 10 mg diclofenac (DF), jet-milled DF, and jet-milled diclofenac sodium (DFNa) carrier-free formulations at 4 kPa pressure drop across high-resistance Monodose RS01

| Formulation | RF % | ED % | FPF % | FPF 5 μm % | FPF 3 μm % | FPF 1 μm % | MMAD | GSD |
|---|---|---|---|---|---|---|---|---|
| Jet-milled DFNa | 32.9 ± 1.0 | 43.6 ± 0.8 | 75.6 ± 3.3 | 75.9 ± 3.3 | 72.0 ± 3.8 | 34.0 ± 3.0 | 1.9 ± 0.1 | 2.0 ± 0.0 |
| Jet-milled DF | 41.7 ± 3.5 | 68.9 ± 2.9 | 60.4 ± 2.8 | 60.8 ± 2.8 | 43.0 ± 1.5 | 8.6 ± 0.6 | 3.1 ± 0.1 | 2.1 ± 0.0 |
| DF | 30.3 ± 5.1 | 80.3 ± 3.5 | 38.4 ± 5.7 | 38.4 ± 5.7 | 22.5 ± 1.9 | 3.9 ± 0.6 | 4.2 ± 0.1 | 2.2 ± 0.1 |

In the current study, DF free acid was precipitated due to its pH-dependent solubility from an aqueous solution of DFNa according to the following formulas:

Diclofenac sodium→Diclofenac⁻(aq)+Na⁺   Equation (12)

HC→H⁺—Cl⁻   Equation (13)

Diclofenac⁻(aq)+H⁺→Diclofenac(s)   Equation (14)

the 938.39 cm⁻1 peak corresponding to the O—H bending and the ~3320 cm⁻1 peak is associated with the O—H stretching, a bond present in the free acid, but not the sodium salt, thereby confirming the formation of DF free acid from DFNa. Finally, the X-ray diffractogram for DF was compared to the literature, and its identity was verified as the free acid.

Through micronization, DFNa went through a six-fold particle size reduction (19.5 to 3.25 µm); however, DF went through an only three-fold particle size reduction (6.98 to 2.36 µm). Differences in crystal strength and brittleness led to the varying extents of particle size reductions observed for DF and DFNa, despite the similar attrition energy used for jet milling. DFNa is an ionic compound with a higher melting point than DF, which is an organic compound with a lower melting point. Therefore, DFNa requires a higher energy input to achieve a similar particle size. Comparisons of the PSD results for DFNa and DF should be interpreted with caution, considering that the dispersion media for the laser diffraction were different due to the water solubility of DFNa compared to the pH-dependent solubility of DF. Furthermore, the starting PSD was much smaller for DF compared to DFNa (e.g., see Table 12). Additionally, PSD analysis by laser diffraction also has limitations for non-spherical particles. The hollow straws of DF have a high aspect ratio, and the assumptions required by the principle of measurement for this instrument may not be valid.

Regarding the characterization of samples (Table 13), jet-milled DF and DFNa possessed an increased SSA compared to DF and DFNa. The abnormally high SSA value of 11.3±0.81 $m^2/g$ for jet-milled DFNa is clearly an overestimation of SSA since jet-milled DF with smaller particle size has an SSA of 2.40±0.21 $m^2/g$. This overestimation of SSA for jet-milled DFNa is due to the possible formation of a multilayer adsorbate and its condensation on the jet-milled DFNa particles. Regarding the true densities, the DF density of 1.48 $g/cm^3$ corresponded to the literature true density for the denser polymorph of DF. The DFNa density of 1.51 $g/cm^3$ seems to be the first report of the true density for DFNa. Higher true densities were calculated for the jet-milled powders; however, that can be attributed to the low sample mass, the moisture content, and the smaller particle size of the powder. An improved angle of repose, as an indicator for improved flow properties of DFNa following jet milling, can be due to the agglomeration and the moisture content of the micronized powder. On the other hand, the similar angle of repose for the DF powder following jet milling can be attributed to the small initial size of the DF particles ($D_{50}$=6.98 µm) and the presence of agglomerates before jet milling. Following jet milling, HR and CI calculations of flow showed worsening flow for DF; however, they showed improved flow from very poor to fair flow for DFNa.

During jet milling, different percent recoveries in the cyclone, the collection vessel, and the collection bag can be attributed to the smoother, smaller particles of DF compared to DFNa, as the DF particles have a higher degree of adhesion to the surface of the cyclone and cohesion together. Different PSDs for the various segments of the jet mill indicate that particles distribute differently in jet mills as they do in impactors.

There were no detectable transformations of DF and DFNa following jet milling by FT-IR and DSC. Overlapping peaks associated with the FT-IR spectra of DF and jet-milled DF as well as DFNa and jet-milled DFNa signify that following jet milling, the chemical composition of DF and DFNa were not altered. Finally, the similar DSC thermograms for DF, and jet-milled DF, as well as DFNa, and jet-milled DFNa signify that there are no detectable polymorphic changes after the jet milling of DF and DFNa.

Analysis revealed that similar masses of drugs remained in the capsules for DF, and jet-milled DF and DFNa. However, there was a significantly larger mass of jet-milled DFNa deposited in the inhaler base and the mouthpiece compared to DF and jet-milled DF. These differences are not due to the jet-milled DFNa PSD, as its $D_{50}$ value is between the $D_{50}$ value for the DF and jet-milled DF PSDs. Such a deposition difference may be due to the higher moisture content of DFNa as shown in Table 13. Moreover, there were significant differences in the induction port and the pre-separator deposition between the three formulations. Smooth surfaces of the jet-milled DF and DF needles led to increased adhesion to the NGI surfaces and increased cohesion and the agglomeration of particles compared to the rough surface of jet-milled DFNa. Furthermore, the larger particle size of the DF needles compared to jet-milled DF and DFNa may be a contributing factor. Such a difference might also be partly due to the drug entrapment in the inhaler base and the mouthpiece for jet-milled DFNa compared to jet-milled DF. Furthermore, the jet-milled DFNa fines that reach the NGI stages have the smallest MMAD followed by jet-milled DF and DF. Particle size reduction through jet milling for DF yielded a formulation with an overall better in vitro aerodynamic performance as opposed to the unprocessed DF. However, when comparing the RF % for the three formulations, DF and jet-milled DFNa have a comparable RF %. Even though jet-milled DF does not have the smallest MMAD, it is associated with the largest RF % at 41.7%. The DF hollow needles are remarkable as they are relatively long; however, due to being hollow and being needles have a relatively small MMAD and comparable RF % to the jet-milled powders.

The carrier-free formulation of DF with the 3 mg respirable dose (RF %=30%) roughly equals to 10% of the 35 mg mass of commercialized DF currently marketed as Zorvolex® (Iroko Pharmaceuticals, L L C, 2013), the estimated theoretical respiratory dose requirements. In 2013, DF was approved for the first time as a capsule containing 18 or 35 mg of DF free acid under the brand name of Zorvolex with a similar pharmacodynamic profile to the higher doses of DF salts. This formulation of DF contains submicron particles of DF free acid to improve dissolution rate, which is dry-milled using the patented SoluMatrix™ technology, developed by iCeutica Pty. Inc. Particle size reduction was achieved using multiple grinding bodies with diameters of 1-15 mm and aggregation was prevented by adding a grinding matrix, which can be separated before further processing, or be formulated into final formulation.

One can reduce the aerodynamic diameter by manipulating the dynamic shape factor through needle particle engineering and decreasing the particle density through the creation of porous particles. The carrier-free, hollow needle formulation of DF, consisting of particles with a high aspect ratio, possesses both the described attributes and was shown to have a good MMAD and a comparable RF % to jet-milled DF and DFNa. The delivery of the carrier-free formulation to the lung lowers the total dosage requirement and decreases the ADRs associated with the oral delivery of the DF. However, the DF formulation needs to be optimized to minimize the RF % variability and the deposition in the induction port and pre-separator.

DF hollow, crystalline needles were precipitated, characterized, and their in vitro aerodynamic performance was compared to jet-milled DF and DFNa using NGI. Jet-milled DF and DFNa with similar PSDs had different deposition patterns in the NGI. However, the DF hollow needles, with a large aspect ratio, proved to have a comparable RF % to the jet-milled DF and DFNa particles. This carrier-free DPI formulation can reach deep lungs to act locally or systemically, with reduced ADRs by decreasing the total dose requirements.

Although various embodiments of the method and system of the present invention have been illustrated in the accompanying Drawings and described in the foregoing Specification, it will be understood that the invention is not limited to the embodiments disclosed, but is capable of numerous rearrangements, modifications, and substitutions without departing from the spirit and scope of the invention as set forth herein. It is intended that the Specification and examples be considered as illustrative only.

What is claimed is:

1. A method for treating or ameliorating inflammation and/or treating a disease in a subject in need thereof, the method comprising administering a dry powder inhaler composition that consists of a micronized formulation of non-steroidal anti-inflammatory drug (NSAID) particles, wherein the NSAID particles and composition are carrier-free, wherein the NSAID particles consist of pure and excipient-free, undiluted NSAID, wherein the composition has a respirable fraction (RF) value of at least 50% and wherein the NSAID possesses anti-inflammatory and anti-microbial activities, wherein the composition is administered by inhalation delivery to the airways of the subject's lungs.

2. The method of claim 1, wherein the NSAID is jet milled to create a particle size of less than 5 µm.

3. The method of claim 1, wherein the NSAID is jet milled to create a particle size of less than 1 µm.

4. The method of claim 1, wherein the composition is a free-flowing powder.

5. The method of claim 1, wherein the NSAID is jet milled to create an angle of repose of less than 45°.

6. The method of claim 1, wherein the NSAID is ibuprofen, naproxen, diclofenac, or indomethacin.

7. The method of claim 1, wherein the inhalation is facilitated by a nebulizer or a metered dose inhaler.

* * * * *